(12) United States Patent
Nicholls et al.

(10) Patent No.: US 9,816,924 B2
(45) Date of Patent: Nov. 14, 2017

(54) ASSAY DEVICE AND METHODS

(71) Applicant: L3 TECHNOLOGY LIMITED, Ledbury (GB)

(72) Inventors: Anthony Nicholls, Ledbury (GB); Laura Garcia, Ledbury (GB); Mark Hudson, Ledbury (GB); Gareth Jones, Ledbury (GB); David Clarke, Ledbury (GB)

(73) Assignee: L3 Technology Limited, Ledbury (GB)

( * ) Notice: Subject to any disclaimer, the term of this patent is extended or adjusted under 35 U.S.C. 154(b) by 0 days.

(21) Appl. No.: 13/960,824

(22) Filed: Aug. 7, 2013

(65) Prior Publication Data

US 2013/0344581 A1  Dec. 26, 2013

Related U.S. Application Data

(63) Continuation of application No. 13/054,354, filed as application No. PCT/GB2009/050861 on Jul. 15, 2009, now abandoned.

(30) Foreign Application Priority Data

Jul. 15, 2008 (GB) .................................. 0812907.4
May 28, 2009 (GB) .................................. 0909130.7

(51) Int. Cl.
*G01N 21/75* (2006.01)
*G01N 21/64* (2006.01)
(Continued)

(52) U.S. Cl.
CPC ......... *G01N 21/64* (2013.01); *B01F 13/0071* (2013.01); *B01F 13/0084* (2013.01);
(Continued)

(58) Field of Classification Search
CPC ....... B01L 2300/0816; B01L 3/502715; B01L 2300/0887; B01L 2300/165;
(Continued)

(56) References Cited

U.S. PATENT DOCUMENTS 4,226,713 A * 10/1980 Goldberg .................. C12Q 1/60
                                                              210/716
5,132,095 A    7/1992 Koshiishi et al.
(Continued)

FOREIGN PATENT DOCUMENTS

JP      2003230829 A     8/2003
JP      2004061229 A     2/2004
(Continued)

OTHER PUBLICATIONS

Pavlov et al, "New Reagentless Glutamate Biosensors Based on Mesophilic and Thermophilic Glutamate Dehydrogenases" Thesis, Universitat Rovira i Virgili, Jan. 28, 2005.*
(Continued)

*Primary Examiner* — Dennis M White
(74) *Attorney, Agent, or Firm* — Klauber & Jackson LLC

(57) ABSTRACT

The present invention relates to the use of amphipathic polymers to enhance lateral flow and reagent mixing on assay devices. More specifically, the invention relates to use of an amphipathic polymer in assay methods including a device for determining the concentration of lipids in blood serum or plasma.

19 Claims, 5 Drawing Sheets

(51) Int. Cl.
*B01F 13/00* (2006.01)
*B01L 3/00* (2006.01)
*G01N 33/92* (2006.01)

(52) U.S. Cl.
CPC ........ *B01L 3/502769* (2013.01); *G01N 33/92* (2013.01); *B01L 2300/161* (2013.01); *B01L 2400/0406* (2013.01); *B01L 2400/088* (2013.01); *Y02P 20/582* (2015.11)

(58) Field of Classification Search
CPC ........... B01L 3/502792; B01L 2200/04; B01L 2300/0825; B01L 2300/0829; B01L 2200/0642; B01L 2200/0647; G01N 2035/00326; G01N 21/64; G01N 33/92; G01N 2021/0346; G01N 21/6428; G01N 33/54366; G01N 2015/0288; G01N 21/05; G01N 33/5302; G01N 33/54386; G01N 33/4915; G01N 35/1095
See application file for complete search history.

(56) References Cited

U.S. PATENT DOCUMENTS

| | | | |
|---|---|---|---|
| 5,135,716 A * | 8/1992 | Thakore | 422/412 |
| 6,485,982 B1 | 11/2002 | Charlton | |
| 6,596,238 B1 | 7/2003 | Belder et al. | |
| 7,008,799 B1 | 3/2006 | Zimmer et al. | |
| 7,025,935 B2 | 4/2006 | Jones et al. | |
| 7,220,334 B2 | 5/2007 | Anazawa et al. | |
| 2002/0125135 A1 | 9/2002 | Derand et al. | |
| 2003/0059948 A1 | 3/2003 | Hildenbrand et al. | |
| 2006/0110294 A1 | 5/2006 | Engstrom et al. | |
| 2006/0188906 A1 | 8/2006 | Kim et al. | |
| 2006/0198762 A1 | 9/2006 | Uematsu et al. | |
| 2006/0239859 A1 * | 10/2006 | Ohman | B01L 3/502746 422/400 |
| 2006/0285999 A1 | 12/2006 | Timperman | |
| 2007/0017805 A1 | 1/2007 | Hodges et al. | |

FOREIGN PATENT DOCUMENTS

| | | | |
|---|---|---|---|
| JP | 2005091135 A | 4/2005 | |
| JP | 2005249796 A | 9/2005 | |
| JP | 2005331286 A | 12/2005 | |
| JP | 2006226828 A | 8/2006 | |
| JP | 2007524851 A | 8/2007 | |
| JP | 2008082961 A | 4/2008 | |
| WO | 9005182 | 5/1990 | |
| WO | 9114773 | 10/1991 | |
| WO | 01/47637 A1 | 7/2001 | |
| WO | 03/060157 A2 | 7/2003 | |
| WO | 2006/061646 A1 | 6/2006 | |
| WO | 2006061646 | 6/2006 | |
| WO | 2006/074665 A2 | 7/2006 | |
| WO | 2006/102321 A2 | 9/2006 | |
| WO | WO 2007106579 A2 * | 9/2007 | ......... B01F 11/0071 |
| WO | 2008/011486 A2 | 1/2008 | |
| WO | 2008/038597 A1 | 4/2008 | |

OTHER PUBLICATIONS

International Search Report, PCT/GB2009/050861, dated Jan. 21, 2010.
Iwata et al., "Design and synthesis of amphipathic 310-helical peptides and their interactions with phospholipid bilayers and ion channel formation", J Biol Chem, 1994, 269:4928-33.
Negrete et al., "Deciphering the structural code for proteins: Helical propensities in domain classes and statistical multiresidue information in α-helices", Protein Science, 1998, 7:1368-1379.
Grell et al., "Protein design and folding: template trapping of self-assembled helical bundles", Journal of Peptide Science, 2001, 7:146-151.
Chen et al., "Determination of stereochemistry stability coefficients of amino acid side-chains in an amphipathic α-helix", Journal Peptide Research, 2002, 59:18-33.
Cornut et al., "The amphipathic α-helix concept—Application to the de novo design of ideally amphipathic Leu, Lys peptides with hemolytic activity higher than that of melittin", FEBS Letters, 1994, 349:29-33.
Curry et al., "Crystal structure of human serum albumin complexed with fatty acid reveals an asymmetric distribution of binding sites", Nature Structural Biology, 1998, 5:827-835.

* cited by examiner

ASSAY DEVICE AND METHODS

CROSS-REFERENCE TO RELATED APPLICATIONS

The present application is a continuation of U.S. patent application Ser. No. 13/054,354, which is a national stage application of international patent application number PCT/GB2009/050861, which claims priority both from UK patent application number 0812907.4 and UK patent application number 0909130.7.

FIELD OF THE INVENTION

The present invention relates to the use of amphipathic polymers to enhance lateral flow and reagent mixing on assay devices. More specifically, the invention relates to use of an amphipathic polymer in assay methods including a device for determining the concentration of lipids in blood serum or plasma.

BACKGROUND TO THE INVENTION

Lateral flow assay devices and methods are known in the art. Previously, such devices have been developed to test samples that are easily available in large quantities. However, when the test sample is blood or a component of blood, the collection of a large sample is not always possible, particularly at a point of care such as a doctor's surgery.

Generally these devices comprise a lateral flow matrix, for example, nitrocellulose membranes and the like. A sample applied to the matrix flows along the matrix, and one or more analytes within the sample react with one or more reagents within the lateral flow matrix. Typically, at least one of these reagents is immobilized within the matrix allowing any reaction with the analytes to be detected, for example, visually. Unfortunately, variations associated with sample transfer and diffusion of the sample to the membrane result in a flow that is largely uncontrolled and uneven before reaching a test area. This is because such devices rely on capillary action of the fluids alone. Such a reliance on capillary action may have an adverse affect on the accuracy of the device because the amount of analyte and/or label captured across a test area is not consistent. The use of capillary action alone also means that assays are slow because of unreliable fluid wicking. The assays are also unsuitable for small fluid samples, such as in nucleic acid detection, where the membrane may dry before the assay is completed or there may be insufficient fluid to travel the length of the test device.

As such, a need currently exists for a simple and efficient technique for improving lateral flow assays, particularly to allow faster testing whilst enabling low volume tests to be performed.

One area where lateral flow point of care devices would be useful is in the field of cholesterol and blood lipid testing.

It is well known that the concentration of various lipoproteins in the blood is correlated with the risk of an individual developing atherosclerosis. Atherosclerosis is a disease that affects arterial blood vessels and is commonly referred to as a "hardening" or "furring" of the arteries. It is caused by the formation of multiple plaques on the blood vessel walls, in large part due to the accumulation of macrophage white blood cells and promoted by low density lipoproteins. Without adequate removal of fats and cholesterol from the macrophages by high density lipoproteins (HDL), a chronic inflammatory response develops in the walls of the arteries.

Most of the circulating cholesterol in blood plasma is found in three major classes of lipoproteins. Cholesterol and cholesterol esters are water insoluble substances and are therefore carried by these lipoproteins within the circulatory system for eventual utilisation by the cells of the body.

Each of these lipoprotein classes carries varying amounts of cholesterol. Total serum cholesterol is therefore a complex average of the amount that each lipoprotein class contributes to the total lipoprotein concentration of the serum.

Each class of lipoprotein plays a different role in atherosclerosis. High density lipoproteins or HDL are generally regarded as being 'good cholesterol', that is they are anti-atherogenic. In contrast, Low density lipoproteins or LDL are often referred to as 'bad cholesterol' since they are known to be highly atherogenic. Another class of lipoproteins, very low density lipoproteins or VLDL are considered to be slightly atherogenic.

Levels of HDL in the blood have been extensively investigated in view of the inverse relationship between HDL cholesterol and the risk of atherosclerosis and, for example, heart attack. Thus, if the levels of HDL cholesterol are determined to be low, an individual may have an increased risk of developing atherosclerosis. Therefore, this risk can be estimated by assaying HDL cholesterol. From these assay results an approximate amount of LDL cholesterol may be calculated using the following equation:

LDL Cholesterol=Total Cholesterol−⅕ Total Cholesterol−HDL Cholesterol

To determine the cholesterol content of the various cholesterol fractions, generally four methods have been used. These include (1) ultracentrifugation, (2) fractional precipitation, (3) calculation using the Friedewald equation and (4) electrophoretic separation and precipitation.

Each of these methods suffers from a number of drawbacks. For example, ultracentrifugation requires the use of specialised laboratory equipment and may take several days to complete. Fractional precipitation and electrophoretic separation are both time-consuming and again require the use of specialised equipment. The Friedewald equation is inaccurate because it estimates the concentration of LDL cholesterol by subtracting the cholesterol associated with other classes of lipoproteins. Thus, the equation provides an indirect estimation based on three independent lipid analyses each of which provides a potential source of error.

As a result of these drawbacks, the results of cholesterol assays are not available for several hours or even days and cannot be performed in smaller laboratories or by doctors in their surgeries. Accordingly there is a need for a device and method of performing a cholesterol assay that is both simple and inexpensive to use. There is also a need for an assay that directly measures the concentration of each class of lipoprotein without relying on indirect estimates.

When solid hydrophobic molecules are added to an aqueous solution or suspension they form an immediate precipitate and do not enter the aqueous phase because the hydrophobic molecules 'stick' together rather than dissolve. Even with vigorous stirring of the precipitate the number of direct encounters between the hydrophobic molecules and molecules in solution is small. Such interactions may also be thermodynamically unfavourable.

Methods of the prior art involve dissolving hydrophobic molecules in suitable water-miscible organic solvents prior to mixing with an aqueous solution or suspension. On entering the aqueous solution, the hydrophobic molecules are mono-dispersed and therefore have an increased probability of interacting with the molecules already in solution. However, such methods suffer from the drawback that the organic solvent is often toxic or can interfere with enzymatic reactions or fluorescence measurement. Such methods are generally also not suitable for point of care use such as in a Doctor's surgery or clinic.

SUMMARY OF THE INVENTION

The Applicants have made the surprising discovery that by use of amphipathic polymers in an assay system, considerable gains in both the efficiency and/or speed of the assay can be achieved. The Applicant's methods are also applicable to rapidly combining hydrophobic reagents and compounds such as luminophores with analytes, for example lipoproteins, in aqueous solution(s)/suspension(s) without direct application of organic solvents. This method enables the lipoprotein contents of blood, foodstuffs, and the like to be easily quantified by measurement of fluorescence. The use of such methods has also enabled the development of a rapid and inexpensive point of care cholesterol assay system.

In a first aspect of the invention, there is provided an assay device for detecting the presence or quantity of an analyte residing in an aqueous sample, the device comprising: at least one flow path along which an aqueous sample can travel, characterised in that the at least one flow path comprises at least one amphipathic polymer wherein, in use the passage of fluid along the flow path is greater than that expected by capillary action alone.

An amphipathic polymer is a polymer possessing both hydrophilic and hydrophobic properties. Such a compound may also be called an amphiphilic compound or a non-ionic hydrophilic polymer. In particular embodiments an amphipathic polymer is a substance that is soluble both in water and a wide range of organic solvents.

The present invention relates to the use of amphipathic polymers such as polyethylene glycol for promoting and/or controlling lateral fluid flow. The invention may also be utilised to increase the interaction between an aqueous sample and at least one reagent, preferably between hydrophobic luminophores and lipoproteins.

Preferably the flow path is coated with the at least one amphipathic polymer.

Surprisingly it has been found that the amphipathic polymers may be used to coat the surface of, for example, plastics or glass to enhance fluid flow to move and/or mix aqueous solutions, for example with 'dry' components combined within or as layers above or below the coating of amphipathic polymers. The use of amphipathic polymers also has the advantage that lateral flow of fluids is improved, for example, over the traditional 'wicking' with porous materials such as is disclosed in U.S. Pat. No. 6,485,982. Wicking methods of the prior art rely on the use of a support vehicle such as paper or a membrane through which liquid is drawn by capillary action. The use of amphipathic polymers removes the need for a support vehicle which relies solely on capillary action and has the surprising effect that liquids may travel greater distances or at greater speeds, for example, along microtubes or surfaces than in porous materials by capillary action alone.

As used herein, the term "lateral flow" refers to the movement of a fluid on a surface wherein the fluid flows, for example laterally, in a particular direction or along a particular path. Preferably the fluid flows at a greater speed or for a greater distance than that observed by capillary action across a particular material alone. It should be noted that the term "lateral flow" is meant to be descriptive and not limiting, as the device could be configured in other ways with the same effect, for example, radial or vertical flow can easily be envisaged employing the same principles as the present invention, without departure from the spirit of the invention. In particular embodiments the fluid coincidentally interacts with, and analytes contained therein may react with, various reagents as it flows or travels.

The device comprises at least one flow path along which an aqueous sample can travel, and is characterised in that the at least one flow path comprises at least one amphipathic polymer wherein, in use the passage of fluid along the flow path is greater than that expected by capillary action alone. In contrast to the prior art, the device does not require a porous membrane for lateral fluid flow, instead the fluid may travel along the flow path comprising the at least one amphipathic polymer.

Surprisingly it has been discovered that fluids travel faster and/or over greater distances along a flow path comprising an amphipathic polymer than along flow paths comprising porous materials, such as membranes.

In particular embodiments the flow path contains the at least one amphipathic polymer.

Thus, an amphipathic polymer may be used to coat a surface such as the inside of a tube, capillary, channel, well, membrane or the like. It will be apparent that the amphipathic polymer may also be used as a coating for membranes used in 'standard' lateral flow assays to speed up and/or provide greater control over the fluid flow.

In other embodiments the flow path is formed by the at least one amphipathic polymer.

The hydrophobic or amphipathic polymer may be printed and/or sprayed onto a surface, such as a flat surface, for example forming 'tracks' and/or layers, by printing methods such as by inkjet or bubble-jet printing, painting, spraying or other application methods.

The amphipathic polymer may be in the form of a film.

In other embodiments, the film may be ground into particulate material or may be formed into, is for example, granules, beads, pellets, microspheres or nanospheres or picospheres. The amphipathic polymer itself may be in the form of granules, beads, pellets, microspheres, nanospheres or picospheres.

In yet other embodiments the amphipathic polymer may be printed as part of or forming one or more arrays of nano-, pico-, or femto-liter droplets.

Preferably, the amphipathic polymer comprises at least one probe, reporter or reagent. Preferably the reporter is a hydrophobic compound or reagent such as a luminophore.

To combine a hydrophobic compound or reagent with the polymer, said hydrophobic compound or reagent may first be dissolved in a solvent, such as an organic solvent, that is miscible with the amphipathic polymer. The amphipathic polymer is also dissolved in a solvent such as water or a more volatile solvent such as dimethyl formamide or chloroform although other suitable solvents will be readily apparent to one skilled in the art. The hydrophobic compound or reagent and amphipathic polymer are then combined and then preferably dried into a thin film. Surprisingly, the inventors have discovered that on drying, there is no phase separation of the hydrophobic compound or reagent and polymer.

The flow path may comprise at least one probe, reporter or reagent. The flow path may contain the probe, reporter or reagent.

Thus, the combination of at least one hydrophobic luminophore and amphipathic polymer may be used to coat a surface such as the inside of a tube, capillary, channel, well, membrane or the like. In yet other embodiments, the combination may be printed onto a surface, for example forming 'tracks', by printing methods such as by inkjet or bubble-jet printing, painting, spraying or other application methods. The probe, reporter or reagent may be adjacent the at least one flow path. Alternatively, the probe, reporter or reagent may be layered directly above or below the at least one flow path. Thus, the reagents may be within the flow path itself, for example combined with the amphipathic polymer or may be arranged as discrete layers or printed as 'dots' above, below or beside the amphipathic polymer.

It will be apparent that the methods of the invention are also applicable to reagents other than is hydrophobic luminophores, for example, such as enzymes, blocking reagents, chemicals and the like.

Particularly the amphipathic polymer is polyethylene glycol (PEG) with a molecular weight of from about 1000 to 20,000 Da, more particularly between about 1000 to 6000 Da and yet more particularly from about 1000 to 3000 Da. Particular PEGs include PEG2000, PEG6000, PEG12000 and PEG20000.

Polyethylene glycol, also known as polyethylene oxide (PEO) or polyoxyethylene (POE), is an oligomer or polymer of ethylene oxide. PEGs are available over a wide range of molecular weights from 300 g/mol to 10,000,000 g/mol. PEG has the following general structure:

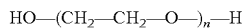

$$HO-(CH_2-CH_2-O-)_n-H$$

Numbers are frequently included in the names of PEGs to indicate their average molecular weights. For example, a PEG with n=80 would have an average molecular weight of approximately 3500 daltons and would be labeled PEG 3500.

Generally PEGs include molecules with a distribution of molecular weights. Whilst PEGs having different molecular weights find use in a variety of applications due to their differing physical properties, such as viscosity, their chemical properties are nearly identical. Different forms of PEG are also available dependent on the initiator used for the polymerization process, such as monofunctional methyl ether PEG (methoxypoly(ethylene glycol)), abbreviated mPEG. PEGs are also available with different geometries. Branched PEGs have 3 to 10 PEG chains emanating from a central core group. Star PEGs have 10-100 PEG chains emanating from a central core group. Comb PEGs have multiple PEG chains normally grafted to a polymer backbone. PEGs may also be covalently coupled to other molecules in a process known as PEGylation which may be advantageous when using the fluid flow properties of PEG for reagent mixing for example.

Further amphipathic polymers may include amphipathic polypeptides, that is, a polypeptide that has a secondary structure such that the polypeptide has both a hydrophilic and a hydrophobic face. The design of amphipathic peptide structures (e.g. alpha-helical polypeptides) is known in the art. For example, in: Grell et al. (2001) J Pept Sci 7(3):146-51; Chen et al. (2002) J Pept is Res 59(1):18-33; Iwata et al. (1994) J boil Chem 269(7):4928-33: Comut et al. (1994) FEBS Lett 340(1):29-33; Negrete et al. (1998) Protein Sci 7(6):1368-79. Other amphipathic or non-ionic polymers include polyvinyl alcohol (PVA) (Sigma Aldrich:360627-25G), Carboxymethyl cellulose (Sigma: C-5678); 0,0'-Bis (2-aminoethyl) PEG 2000 (polyoxyethylene bis(amine)) (Aldrich Chemistry: 14501) and PEG methyl ether 5000 (Aldrich Chemistry: 81323-250G) and other ionic polymers.

Preferably the device further comprises at least one application area for application of an aqueous sample.

An application area is the region on the apparatus wherein the sample is applied. Preferably there is a single application area from which a plurality but at least one, two, three or more aliquots of the sample may be taken for performing assays according to the method of the invention. Alternatively there may be separate application areas for each or different aliquots of sample. It will be appreciated that, in some embodiments, the device may be designed such that the sample may be directly introduced into the test area(s) obviating the need for an application area.

The term "aqueous sample" as used herein refers to any liquid sample, preferably one from which an analyte may be detected. Non-limiting examples of such samples include whole blood, serum or plasma samples, urine, cerebrospinal fluid (CSF), lymph, serous exudate or other biological fluids, animal tissue homogenates, deproteinised tissue homogenates, milk, raw egg, fermentation broths, animal feeds, and marine feeds. It should be appreciated that a sample need only be in liquid or aqueous form for at least an essential part of any assay. Thus, one skilled in the art may envisage that such an assay may also be carried out at temperatures above the melting point of a sample, such as a wax or lipid for example, that is normally solid at room temperatures.

Preferably the device further comprises at least one test area wherein the result and/or progress of a reaction between a part of the aqueous sample and the probe, reporter or reagent is determined.

The test area(s) are region(s) in which the result and/or progress of a reaction between an analyte and probe, reporter or reagent may be determined. The test area(s) may be brought into contact with excitation means.

Preferably at least one flow path is in fluid communication with at least one application area and at least one test area. Preferably, the apparatus comprises a plurality of flow paths and test areas. Preferably the flow path connects, for example by fluid communication, an application area with at least one test area.

The flow path may be a channel, groove, capillary, track or path and the like. Preferably the flow path comprises an amphipathic polymer. The amphipathic polymer may be in the form of a coating or film on the surface of the flow path or may be in the form of a powder, pellets, microparticles, nanoparticles, picoparticles or filling within a cavity of the flow path. Where the amphipathic polymer is a filling within a cavity it may fill the cavity entirely or may be a partial filling with, for example, gaps. Alternatively, the amphipathic polymer may be the flow path, for example, provided as a track or path, for example, printed on a surface along which fluid lateral flow occurs.

The flow path which comprises the amphipathic polymer may further comprise other reagents required for the assay(s), for example, at least one hydrophobic luminophore and/or at least one enzyme. Different flow paths may comprise different reagents. A flow path may also comprise different reagents along its length, for example, allowing for sequential addition of reagents through lateral flow of the aqueous sample. Alternatively the flow path comprises the amphipathic polymer alone leading to a test area(s) that comprises the amphipathic polymer in combination with other reagents. The reagents may be within the flow path itself, for example combined with the amphipathic polymer or may be arranged as layers above, below or beside the amphipathic polymer.

Preferably the result and/or progress of a reaction is determined by means of optical measurement. Alternatively the result and/or progress of a reaction is determined by visual inspection. More particularly the result and/or progress of a reaction is determined by means of fluorescence.

Thus it is preferred that the test area is arranged so that it may be brought into optical contact is with excitation means. The test area should be arranged such that fluorescence produced from the assay may be detected by the detection means. There may be separate test areas for different aspects of the same assay or for different assays. "Excitation means" are means operable to excite the sample so that at least one component of the sample—usually a probe or reporter—fluoresces.

Use of the term 'contact' above is not intended to imply or limit to physical contact, in this context the term may simply mean that the test area(s) is physically moved into the path of a beam of light or that the test area is illuminated/excited by a beam of light.

Detection means are means operable to detect fluorescence emitted by the sample. In particular embodiments, measurement may be performed simply by visual checking. In this instance, excitation means and detection means may not be necessary.

In particular embodiments the device comprises at least two separable components. More preferably the at least two separable components are a reader and a test cartridge. Thus, the apparatus may comprise two or more separate components, for example, a reader and a cartridge adapted to be placed in functional communication with the reader. Preferably, the cartridge may be inserted into, placed on or attached to the reader. The reader may comprise docking means in which the cartridge is inserted, placed or attached. The docking means may be a slot. Hence, preferably, the cartridge is removable from the reader. The cartridge may take a variety of forms, for example, a card, chip or slide, and be constructed from materials known in the art, for example, cardboard, glass, silicon, plastics and the like. Preferably the material comprises, or is, a hydrophobic material or has regions that are hydrophobic.

Preferably the test cartridge comprises the at least one flow path. Preferably the test cartridge is a disposable and may be replaced with a new cartridge containing new assay reagents.

Preferably the reader is a re-usable component.

In preferred embodiments the device is an assay device for detecting the presence or quantity of an analyte residing in an aqueous sample comprising:
(i) at least one application area suitable for application of an aqueous sample to the device;
(ii) at least one probe, reporter or reagent wherein, in use the at least one probe, reporter or reagent is able to react with an analyte residing in the aqueous sample;
(iii) at least one test area wherein, in use the result and/or progress of a reaction between the analyte and the at least one probe, reporter or reagent may be determined;
(iv) at least one flow path being in fluid communication with the at least one application area and the at least one test area,
characterised in that the at least one flow path comprises at least one amphipathic polymer and wherein, in use the passage of fluid along the at least one flow path is greater than that expected by capillary action alone.

In particular embodiments the apparatus comprises a single application area and a plurality of flow paths, for example four, leading to a plurality, for example at least three, test areas.

When the device comprises at least three test areas and at least three flow paths preferably, a first flow path is in fluid communication with the application area and a first test area, a second flow path is in fluid communication with the application area and a second test area and a third flow path is in fluid communication with the application area and a third test area.

In one embodiment the first flow path and/or test area comprises the amphipathic polymer in combination with a first hydrophobic luminophore and optionally at least one enzyme. A second flow path and/or test area comprise the amphipathic polymer in combination with a second hydrophobic luminophore and optionally at least one enzyme. The third flow path and/or test area comprises the amphipathic polymer in combination with either the first, second or a third hydrophobic luminophore and optionally at least one enzyme. In use the sample (in aqueous form) applied to the application area is urged along the at least one flow path into the respective test area(s) by lateral flow effected by the amphipathic polymer. As the sample flows along the at least one flow path it is presented and mixed with the hydrophobic luminophore and/or other reagents. Alternatively, the sample is only presented with the hydrophobic luminophore and/or other reagents when it reaches the test area. Preferably the sample moves by lateral flow not requiring external forces, such as pumps, to move the aqueous sample. Once the aqueous sample reaches the test area(s) measurements may be taken.

Where the assay is a lipid profiling assay the probe, reporter or reagent may be selected from the group consisting of Amplex Red, K37, Nile Red, cholesterol esterase, cholesterol oxidase or horseradish peroxidase.

Amplex Red (10-acetyl-3,7-dihydroxyphenoxazine), available from Invitrogen (catalogue numbers A12222 and A22177) amongst others, reacts with Hydrogen peroxide ($H_2O_2$) with a 1:1 stoichiometry to produce highly fluorescent resorufin. K37 (4-dimethylamino-4'-difluoromethyl-sulphonyl-benzylidene-acetophone) is disclosed by the inventors in their previous International patent application PCT/GB2005/004757. Nile Red a lipophilic stain, also known as Nile blue oxazone, is available from Invitrogen (catalogue number N1142) or may be produced by boiling a solution of Nile blue with sulphuric acid. Nile red stains intracellular lipid droplets red and is also intensely fluorescent, with a strong yellow-gold emission when in a lipid-rich environment.

Cholesterol esterase (Steryl-ester acylhydrolase, Registry number: EC 3.1.1.13) is an enzyme that catalyses the hydrolysis of cholesterol ester and some other sterol esters, to liberate cholesterol plus a fatty acid anion. Cholesterol oxidase (Cholesterol:oxygen oxidoreductase, Registry number: EC 1.1.3.6) is an enzyme that catalyses the oxidation of cholesterol in the presence of molecular oxygen to 4-cholesten-3-one and hydrogen peroxide. Horseradish peroxidise (Sigma Aldrich, Registry number: EC 1.11.1.7) is a Hydrogen peroxide oxidoreductase. Other equivalent hydrogen peroxide oxidoreductases are known and may be derived from, for example, soy bean.

For lipid profiling a first flow path comprises Amplex Red, a second flow path comprises K37 and a third flow path comprises Nile Red. Alternatively the first test area may comprise Amplex Red, the second test area may comprise K37 and the third test area may comprise Nile Red. Yet more preferably, when the first flow path comprises Amplex Red, the first flow path further comprises cholesterol esterase, cholesterol oxidase and horse radish peroxidise. In alternative embodiments the first test area may comprise cholesterol esterase, cholesterol oxidase and horse radish peroxidise. In yet other embodiments the application area comprises the at least one probe, reporter or reagent selected from the group consisting of Amplex Red, K37, Nile Red, cholesterol esterase, cholesterol oxidase or horse radish peroxidise.

Preferably the probe, reporter or reagent is in dry form.

Advantageously, the apparatus may be used to carry out quick and easy assays that can be conducted simultaneously, in parallel, to determine the presence/absence or concentration of an analyte from the biological fluid. For example, the use of an amphipathic polymer reduces the time an assay takes from several hours or even days to around as little as one minute.

In another aspect of the invention there is provided a method of measuring an analyte in an aqueous biological sample comprising:
(i) contacting the aqueous biological sample with a combination of at least one hydrophobic luminophore and at least one amphipathic polymer wherein, the at least one hydrophobic luminophore binds to at least one analyte in the aqueous biological sample and when bound thereto fluoresces under appropriate excitation;
(ii) exciting the product(s) from step (i) at a suitable excitation wavelength;
(iii) measuring the fluorescence emission following step (ii) at a suitable detection wavelength.

It will be apparent to one skilled in the art that suitable excitation and emission wavelengths will be dependent on the particular dye or luminophore used. Selection of suitable wavelengths may be determined using standard laboratory techniques or available data relating to the dye or luminophore.

In one embodiment of the method of the invention, the aqueous biological sample is contacted to with the at least one amphipathic polymer before contacting with at least one hydrophobic luminophore.

In an alternative embodiment, the aqueous biological sample is contacted with the at least one amphipathic polymer at substantially the same time as it is contacted with at least one hydrophobic luminophore.

By way of non-limiting example, the biological sample (in aqueous form) is applied to an application area on, for example, a test chip or card according to the first or second aspects of the invention. The application area is connected to at least one, preferably three, four or more test areas. The connection between the areas may be by channels, capillaries, tracks and the like. The channels, capillaries and the like are preferably coated with an amphipathic polymer. Where tracks are used, they may be formed from an amphipathic polymer, for example, printed or laid down onto a surface. The amphipathic polymer 'wicks' or draws the aqueous sample from the application area, along the channels, capillaries, tracks and the like, to the at least one test area. Where multiple channels, capillaries, tracks and the like are used, the sample may be divided or split into aliquots as the fluid travels along them. In this manner the sample may be divided without manual processing steps through the use of lateral flow effected by the amphipathic polymer.

Each channel, capillary, track and the like may comprise at least one hydrophobic luminophore in combination with the amphipathic polymer. Where present, the hydrophobic luminophore in each channel, capillary track and the like may be the same or a different. Each different hydrophobic luminophore may bind to a specific class or subclass of lipoproteins and when bound thereto, modifies the fluorescence yield under appropriate excitation, which is indicative of the concentration of the specific class or sub-class of lipoproteins. Similarly, each channel, capillary or track and the like may also comprise at least one enzyme or other component or reagent. In this manner, as the sample travels or flows (is drawn) along the channels, etc., it is presented and mixes with other components or reagents without the need for manual processing steps. It will be apparent to one skilled in the art that, as a result, different quantities or combinations of reagents or conditions may be applied to different aliquots of the sample resulting in different assays being performed and measured in each test area.

Preferably the at least one hydrophobic luminophore is a dye, more particularly a fluorescent dye and yet more particularly a dye that is uniquely fluorescent when it is bound to an analyte such as a lipid component.

Human Serum Albumin (HSA) is a major component of blood serum having a concentration of approximately 30-50 mg/ml. HSA is known to have at least two types of binding site that are capable of binding various ligands. A first type is referred to herein as "a hydrophobic domain" whereas a second type of domain is referred to herein as a "drug binding domain". These domains are known to one skilled in the art and are distinguished from each other in a paper in Nature Structural Biology (V5 p 827 (1998)). This paper identifies a hydrophobic domain as one to which fatty acids may bind whereas the drug binding domain is capable of binding a number of drugs that may be associated with HSA.

The inventors have established that hydrophobic luminophores may bind to hydrophobic binding sites/domains of HSA and may fluoresce when bound to HSA. Therefore, the inventors believe that this additional fluorescence may cause a substantial background signal, potentially distorting measurements and leading to errors in the determination of concentration of lipoproteins.

Thus, when the aqueous sample is a blood sample, the hydrophobic binding sites of HSA at which hydrophobic luminophores may bind, are blocked. Thus, prior to analysis of a sample a ligand binding inhibitor is preferably added.

The ligand binding inhibitor may be hydrophobic. The inhibitor may be amphipathic. The ligand binding inhibitor may comprise a fatty acid or a functional derivative thereof, as well as other hydrophobic molecules. Examples of suitable derivatives of fatty acid, which may block the hydrophobic binding sites of HSA may comprise a fatty acid, its esters, acyl halide, carboxylic anhydride, or amide etc. A preferred fatty acid derivative is a fatty acid ester.

The fatty acid or derivative thereof may comprise a C1-C20 fatty acid or derivative thereof. It is preferred that the fatty acid or derivative thereof may comprise a C3-C18 fatty acid or derivative thereof, more preferably, a C5-C14 fatty acid or derivative thereof, and even more preferably, a C7-C9 fatty acid or derivative thereof. It is especially preferred that the ligand binding inhibitor comprises octanoic acid (C8) or a derivative thereof, for example, octanoate: Preferably, the ligand binding inhibitor is added as an alkali metal octanoate, preferably a Group I alkali metal octanoate, for example, sodium or potassium octanoate.

Preferably, between about 10-400 mM of the ligand binding inhibitor is added to the sample prior to analysis, more preferably, between about 20-200 mM, and even more preferably, between about 30-80 mM is added. It is especially preferred that about 50 mM of the inhibitor is added.

Hence, in a preferred embodiment of the method, about 50 mM of sodium octanoate may be added to the sample before analysis.

Ligands for the drug binding domains of HSA include drug molecules such as: thyroxine, ibuprofen, diazepam, steroid hormones and their derivatives (drugs), haem, bilirubin, lipophilic prodrugs, warfarin, coumarin based drugs, anaesthetics, diazepam, ibuprofen and antidepressants (e.g. thioxanthine), benzoic acid or a derivative thereof (e.g. trichlorobenzoic acid or triiodobenzoic acid). Alternatively the HSA binding domains may be blocked or removed by use of a HSA extraction means, for example, anti-HSA antibodies.

In particular embodiments the aqueous sample is used 'neat', that is, without dilution of the sample prior to use.

In other embodiments, the aqueous sample may be diluted before use. For example, when the aqueous sample is derived from blood, dilution of the sample may be desirable, for example using a 1 in 80 dilution, before the assay is performed. Preferably the diluent is phosphate buffered saline (PBS) and comprises at least one ligand binding inhibitor. In particular embodiments, the diluent comprises two ligand binding inhibitors, one for the hydrophobic binding site(s) and one for the drug binding site(s). Preferably the ligand binding inhibitors comprise benzoic acid and octanoic acid. Alternatively, the sample may be diluted with PBS and the at least one ligand binding inhibitor is combined with the amphipathic polymer. Thus, the ligand binding inhibitor is added to and mixed with the aqueous sample as it travels by lateral flow, for example, along the tube, capillary, channel or track.

In a preferred method a plurality of, and at least two or three, fluorescence assays are carried out under similar conditions in parallel.

According to a third aspect of the invention there is provided a process for enhancing lateral fluid flow comprising coating a surface along which a fluid may flow with an amphipathic polymer.

Preferably in the process of the invention, the surface is defined by a tube, capillary, channel, well, membrane or the like.

Thus, an amphipathic polymer may be used to coat a surface defined by the inside of a tube, capillary, channel, well, membrane or the like, for example. It will be apparent that the amphipathic polymer may also be used as a coating for membranes used in 'standard' lateral flow assays to speed up and provide greater control over the fluid flow. The hydrophobic or amphipathic polymer may be coated, printed and/or sprayed onto a surface for example forming 'tracks' and/or layers, by printing methods such as by inkjet or bubble-jet printing or other application methods. In particular embodiments of the process the amphipathic polymer is in the form of a film. In other embodiments, the film may be ground into particulate material or may be formed into, for example, granules, beads, pellets, microspheres, nanospheres or picospheres. The at least one amphipathic polymer may be in the form of granules, beads, pellets, microspheres, nanospheres or picospheres.

According to a fourth aspect of the present invention, there is provided the use of Gafquat for stabilisation of a protein, in particular an enzyme.

Surprisingly it has been discovered that co-polymers of vinylpyrrolidone and dimethylaminoethyl methacrylate, sold by International Speciality Products under the trade name Gafquat®, for example, are suitable enzyme stabilising reagents. Gafquat (CAS Registry Number: 53633-54-8; 7732-18-5) is the name for a range of water-soluble copolymers such as Polyquaternium-11. It is the primary active ingredient in many hair products such as mousses, gels, hairsprays and in special effects makeup but has not been used before for the purposes of stabilisation on an enzyme or protein. Preferred enzymes for stabilisation with Gafquat include cholesterol esterase, cholesterol oxidase and horseradish peroxidise although Gafquat may be utilised for stabilisation of a wide range of enzymes.

According to a fifth aspect of the invention there is provided use of the device, method or process of the invention in an assay.

All of the features described herein (including any accompanying claims, abstract and drawings), and/or all of the steps of any method or process so disclosed, may be combined with any of the above aspects in any combination, except combinations where at least some of such features and/or steps are mutually exclusive.

BRIEF DESCRIPTION OF THE DRAWINGS

The invention is described with the help of the following figures, though not limited thereto. It should be understood, that the figures are for illustrative purposes only.

DETAILED DESCRIPTION OF THE INVENTION

Figure 1:
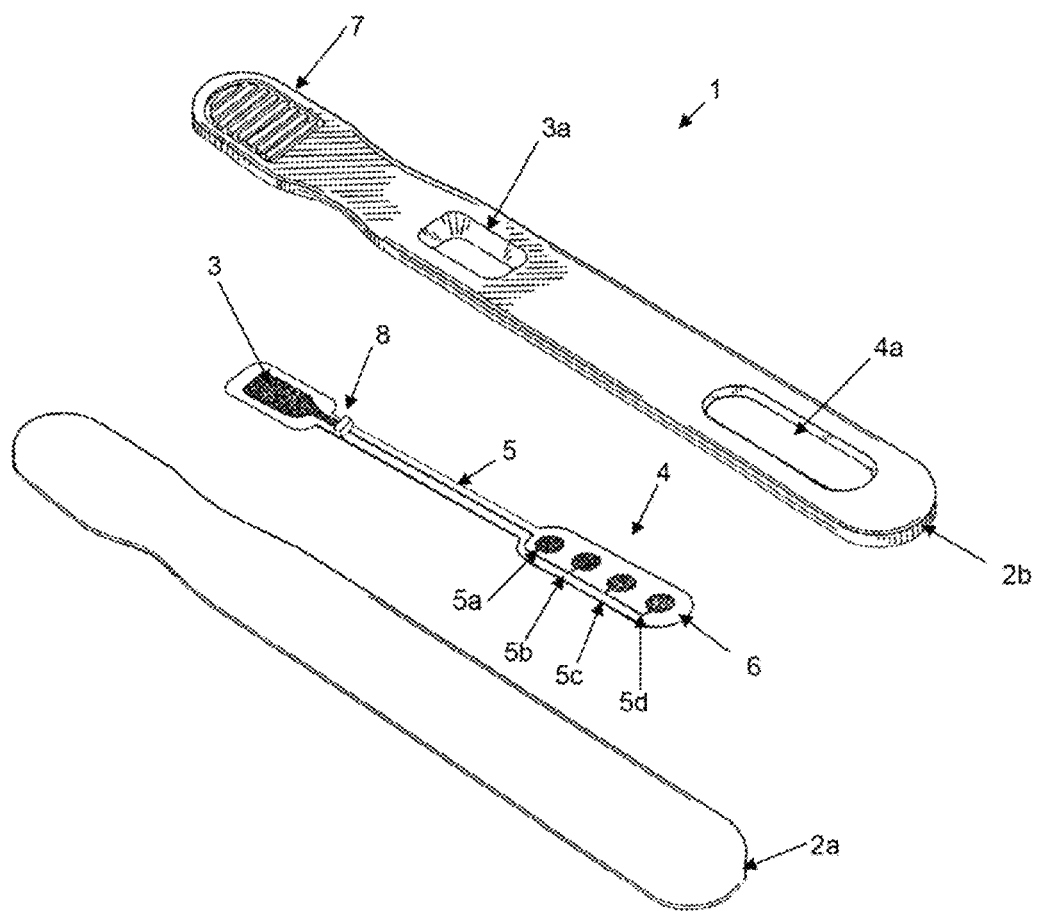
FIG. 1 shows the components of an embodiment of a test cartridge suitable for point of care use.

Referring to FIG. 1 of the drawings, an assay device (1) generally comprises a housing having a base (2a) and a cover (2b) which protects the application area (3), flow paths (5) and test areas (4) from contamination or damage.

The device is provided with a ridged handle portion (7) enabling a doctor or clinician to hold the device. The housing over the application area (3) comprises a well (3a), in this case, having sloping sides to guide the sample onto the application area. A window (4a) provides access to the test areas allowing the results of the assay to be determined.

Within the housing (2a and 2b) is a strip of hydrophobic plastic (6) which acts as a support for the PEG flow paths. The flow paths (5) are printed onto the support leading from the application area (3) to, in this instance, four test areas (4). A filter (8) is glued onto the support to filter particulates from the aqueous sample.

In use, a doctor or clinician applies an aqueous sample to the application area (3). Fluid from the aqueous sample travels by lateral flow along the flow path toward and through the filter (8). The filter, which has been coated with PEG, blocks any cells in the sample from travelling further along the flow paths. Once the fluid approaches the test areas, junctions formed in the is flow path split the sample into four aliquots.

When utilised in the preparation of a lipid profile, as the first aliquot travels along flow path 5(a), it is presented with and mixes with K37 dye combined with the PEG in the flow path. The second aliquot travels along flow path 5(b) and is mixed with a second dye, Nile Red. The third aliquot travels along flow path 5(c) and as it does so, it mixes with three dried enzymes, cholesterol esterase, cholesterol oxidase and horse radish peroxidise and a dye, Amplex Red. Each of the three aliquots of sample, mixed with the respective dyes flows into and collects in the test areas (4). The fourth test area (5d) is used as a control to measure background fluorescence.

The device is loaded into a reader which excites each of the test areas in turn and measures any subsequent fluorescence emission. The processing chip within the reader calculates the concentration of analytes (such as total cholesterol, triglycerides, HDL and other lipid components) within the sample and displays the results on an LCD screen.

Figure 2A:
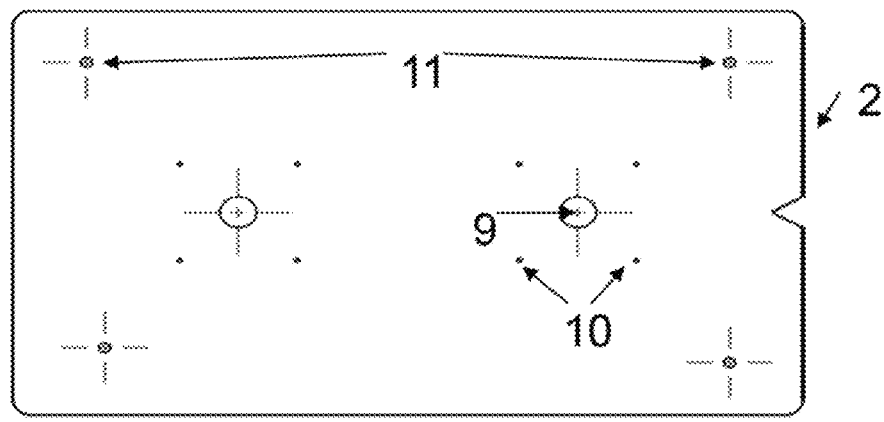
FIGS. 2A, 2B, 2C, 3A and 3B illustrate further embodiments of an assay device
Figure 2B:
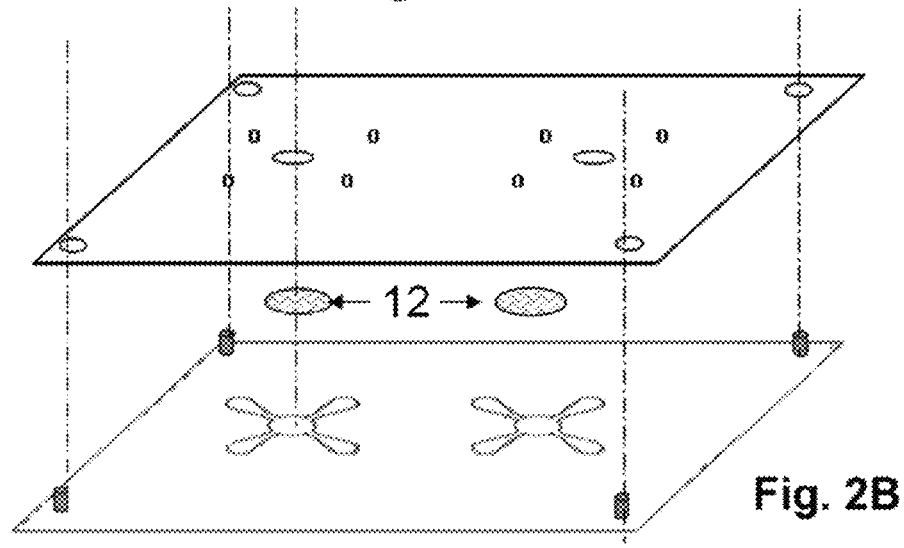
Figure 2C:
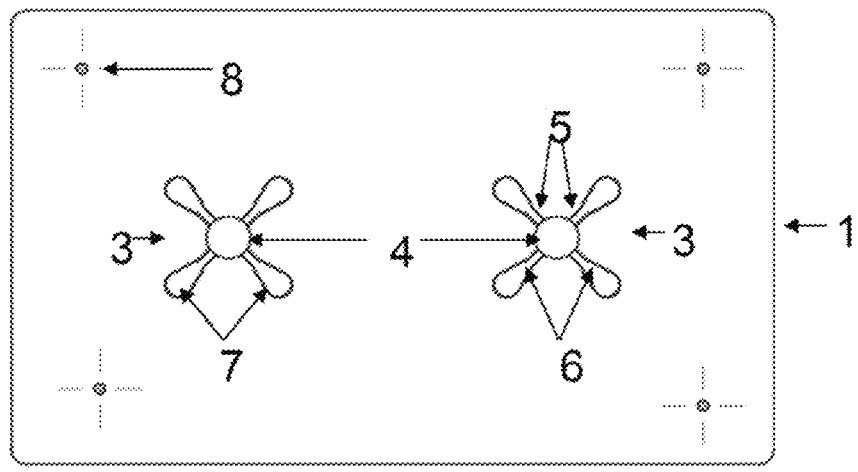
Figure 3A:
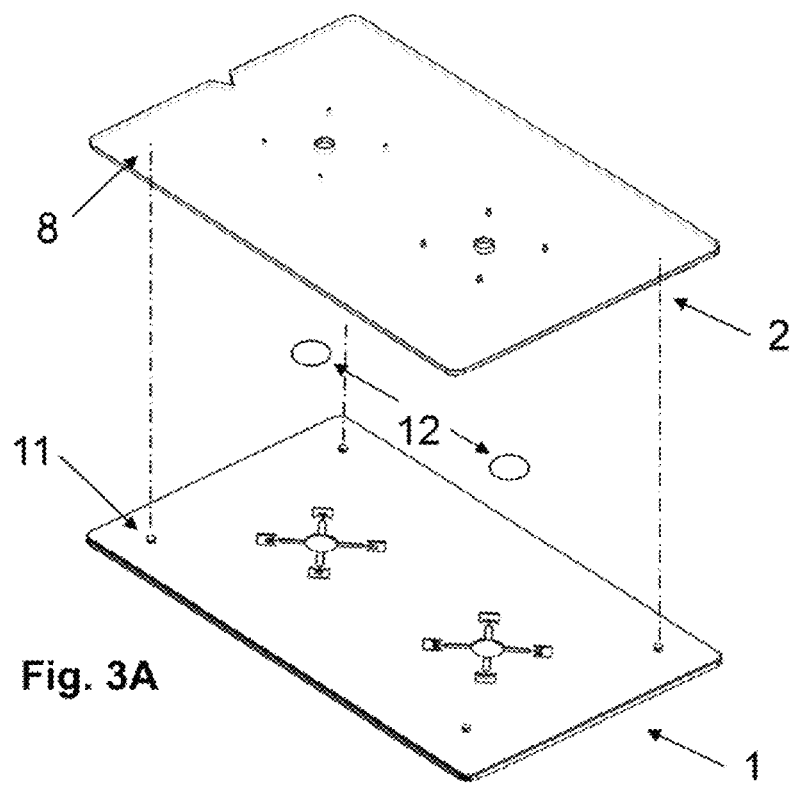
Figure 3B:
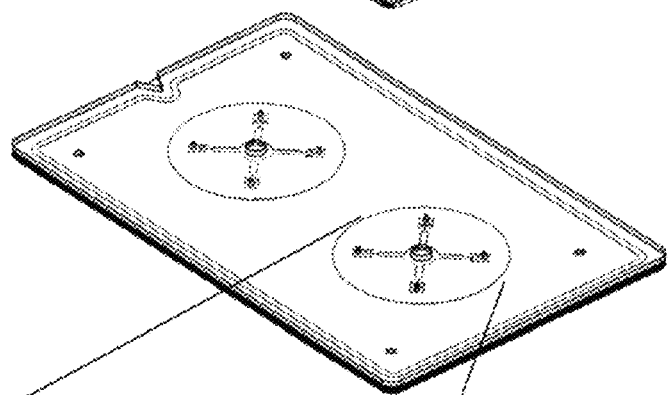
Figure 3B:
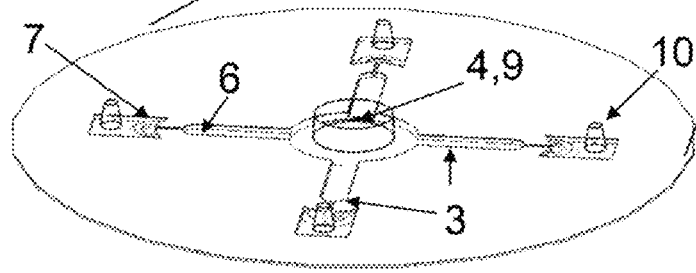

FIGS. 2 and 3 illustrate further embodiments of an assay device according to the invention which may be used, for example, in the determination of lipoprotein levels in blood.

In this embodiment, the assay device comprises a first, support surface (1). The support surface generally comprises or consists of an opaque material, for example a plastics material incorporating an amount of a pigment such as carbon black. In this case, a support surface is formed from a medical grade polymer compatible with fluorescent, luminescent or photometric measurement. Cyclic olefin polymers generally have excellent mechanical properties, low autofluorescence and high UV transmission. Suitable polymers include cyclic olefin copolymers such as Topa® COC (CAS number 26007-43-2), Zeonor® COP, Zeonex® COP or Udel® polysulfone (CAS Number 25135-51-7). In this example the support is formed of TOPAS COC comprising 1% Carbon black. The use of carbon black has the added advantage that, during to laser welding for example, the power requirement is reduced increasing ease of manufacture of the device and protecting heat labile components in the reaction chambers. The use of Carbon black may also have benefits relating to heat dissipation/insulation.

The support surface of this embodiment is moulded but may be formed by any standard is moulding or machining techniques known in the art. Whilst it is generally flat, it comprises profiled areas, in this example of sunken-relief which form, in this case four, capillary channels (3) arranged circumferentially around an application area (4). In this case each of the four channels are equidistantly spaced from one another at an angle of around 90°.

The moulded support surface forms an application area (4), fluid flow paths (5) and detection zones (6).

Figure 4A:
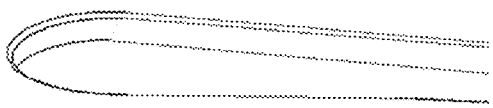
FIGS. 4A, 4B and 4C illustrate embodiments of a capillary channel defining an application area, fluid flow pathway, detection zone and stop-flow junction.
Figure 4B:
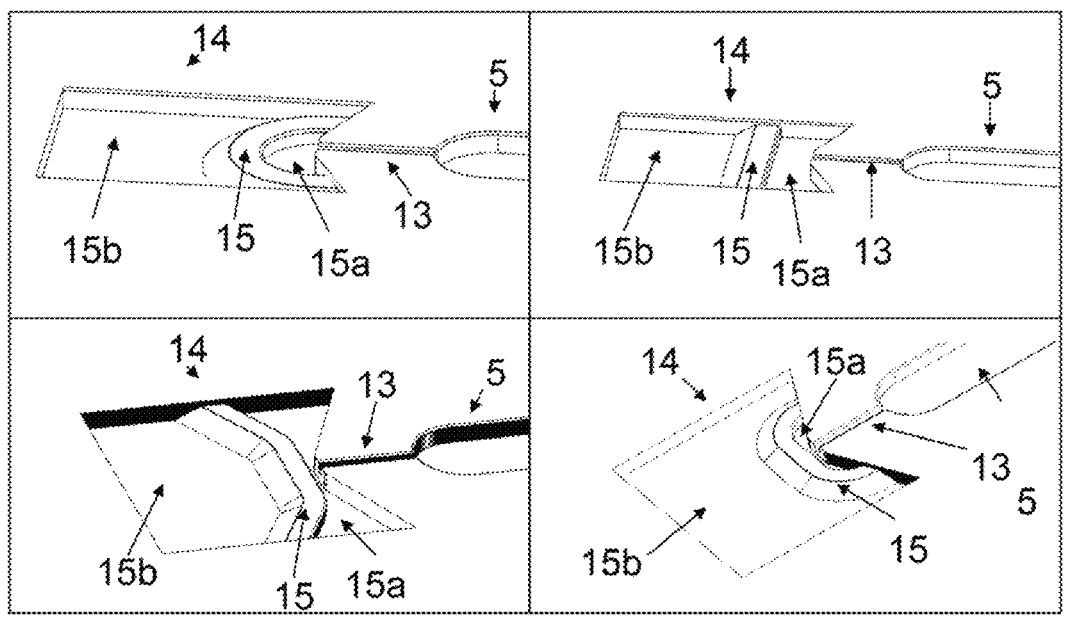
Figure 4C:
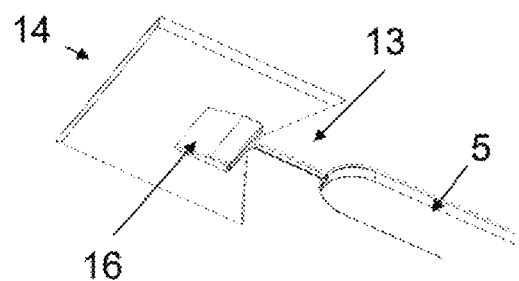

Each end of the fluid flow pathways (5) farthest from the application area (4) is characterised by a gradual taper of one or more of the capillary channel walls. This taper increases the width and/or depth and by extension the cross-sectional area of the capillary flow channel forming a stop flow junction (7) preventing further capillary fluid flow. Here, the channel forms a bulbous end but may take a variety of other forms. The structure of the capillary channel which defines the application area, fluid flow pathway, detection zone and stop-flow junction is shown more closely in FIG. 4. It will be apparent to one skilled in the art that the channels may be arranged in any number of formats or be of differing shapes to suit a particular assay. For example, and by way of non-limiting example, the channels may be ovoid or 'teardrop' shaped, trapezoidal, triangular, columnar or tubular. Further examples, are shown in FIG. 4. For hospital, laboratory or large volume use, it is conceivable that 10-20, 20-40. 40-60 or 50-100 capillary channels could be arranged on an assay device the size and shape of a compact disc.

FIG. 4 illustrates further embodiments of stop flow junctions. In this figure the fluid flow pathway (5) maintains an even cross-sectional area along substantially its entire length before narrowing or constricting to form a section of fluid flow pathway of reduced cross-sectional area (13) towards the distal end. This section of fluid flow pathway is in turn adjacent to, and in fluid communication with a chamber (14). The chamber is divided into regions by a low wall or barrier (15)—in this case into two parts (15a) and (15b). In use, a fluid enters the chamber (14) filling part (15a). The wall (15), or more accurately the capillary forces acting on the sample fluid in the region of the wall, stops flow of fluid into the second part of the chamber (15b). In other embodiments the wall is replaced by a raised portion (16). Again, capillary forces acting on the sample fluid in the region of the raised portion (16), prevents fluid from filling the whole of the chamber. One skilled in the art will realise that the configuration (for example size, shape, height) of the chamber (14) and wall (15) or raised portion (16) may take a number of forms including different geometric shapes such as circles, trapezoids and the like. A vent port located adjacent to the second part or distal region of the chamber (15b) allows for movement of air from within the chamber to the atmosphere equalising pressures within the fluid flow pathways of the device.

The support surface also comprises a number of alignment posts (8) to align the support surface with the second surface—the cover member (2).

The cover member (2) is also formed from a suitable medical grade polymer such as those described above. In this example the cyclic olefin copolymer (Topas COC), CAS number 26007-43-2 was used again but in this case without carbon black. As a result the cover member is optically clear/transparent—at least to the excitation/emission wavelengths of the assay reader.

The cover member (2) is also moulded and generally flat comprising a number of apertures. The cover member is mountable with the support member, optionally comprising a gasket or spacer element positioned there between. Aperture (9) is aligned with the application area and allows a user to apply a fluid sample to the application area. A further series of smaller apertures function as vent openings (10).

In the embodiments shown, alignment holes (11) orientate the cover member with respect to the support member by accommodating the alignment posts (8). In alternative embodiments the apertures and alignment holes are provided in the support member, the cover member simply fulfilling the role of a cover.

The Alignment elements may simply be raised members with corresponding alignment holes or to grooves. The support and cover members may be fixed or bonded together for example by mechanical means such as by use of screws, rivets, bolts or tabs. Alternatively the support and cover members may be held together by friction fit. In other embodiments the cover and support members are bonded together, for example by use of glues, solvents, adhesive tape and the like. In this case the cover and support members are bonded together by use of heat and laser welding.

One or both of the support and cover members may comprise identification means, to provide a unique identifier and/or to provide a means for an assay reader, for example, to monitor the number of times an assay device has been used or when sample was applied so that an appropriate assay time passes. Such identification means may also contain instructions or data such as calibration or quality control data. Identification means may take a variety of forms including, but not limited to, text, Braille, numerical data, linear bar code(s), 2D bar code(s), RFID tag(s) and the like.

A filter (12) is held firmly between the support and cover members adjacent to and in fluid communication with the application area (4) and aperture (9) and the fluid flow pathways.

In use, either an undiluted or diluted aqueous sample is applied directly to the filter via aperture (9).

Fluid in the sample migrates through the filter and as it does so large particulates are removed by passive filtration. In the case of whole blood, such particulates include red blood cells. As a result background interference from such large particulates is reduced.

When used with blood, for example whole, venous, blood, the filter may further comprise an HSA extraction means comprising anti-HSA antibodies which remove HSA from the sample as previously discussed, again reducing background. Blood may be obtained by finger prick or in the case of neonates, a heel prick. This is a way of opening a small wound, for example in the finger tip, which produces no more than a few drops of blood (~less than 50 µl such as from about 10 µl to 20 µl). After a blood droplet has formed it can be applied directly to the application area of the assay device or sucked up by a pipette and then applied accordingly. Other means of obtaining a blood sample are known in the art. The ability to utilise blood obtained by, for example a finger prick, directly represents a significant advantage over assays known in the art.

Alternatively the assay device may be utilised to test a sample that is derived from plasma, in which case a 1 in 80 dilution of the sample may be performed. Generally the diluent that is used is phosphate buffered saline (PBS) and it may comprise at least one ligand binding is inhibitor. The diluent may also comprise two ligand binding inhibitors, one for the hydrophobic binding site(s) and one for the drug binding site(s).

The fluid travels by means of capillary flow from the application area (4) into the fluid flow pathways (5) with which the application area is in fluid communication. As it travels the liquid hydrates reagents in dry form, such as fluorescent dyes and enzymes, and mixes with them. Thus, the sample moves by capillary or lateral flow not requiring the application of external forces, such as pumps, to move the aqueous sample. The amphipathic or non-ionic polymer enhances capillary flow and the efficiency of reagent mixing.

Use of the term 'dry form' refers to components that are maintained in a form in which they are generally substantially free from, or depleted of, liquid or moisture; that is they are not in solution until reconstituted by the performance of the assay itself, rather than being reconstituted prior to and separate from the assay procedures. Thus, the aqueous sample itself reconstitutes the dry reagent or reagents, thereby eliminating the need for separate reconstitution buffers and steps. As described above, use of the amphipathic or non-ionic polymer assists mixing of dry reagents with the aqueous sample.

Where enzymes or other reagents are used, particularly where they are used in dry form, it is preferred that such enzymes or other reagents are stabilised. In the context of this invention, a 'stabilised reagent' is a reagent that has improved stability with respect to, for example, storage stability, thermal stability etc. Thus, in particular embodiments the reagents that are used comprise a stabilising agent. Particular stabilising methods are disclosed in International Patent Application numbers WO90/005182 and WO91/014773 the contents of which are hereby incorporated by reference. Other suitable stabilising reagents include co-polymers of vinylpyrrolidone and dimethylaminoethyl methacrylate, for example, sold by International Speciality Products under the trade name Gafquat®. Gafquat (CAS Registry Number: 53633-54-8; 7732-18-5) is the name for a range of water-soluble copolymers such as Polyquatemium-11.

As the fluid front moves forward, an equivalent volume of air is displaced through the vent openings equalising pressure within the device. Once the fluid reaches the stop-flow junction, is surface tension prevents further capillary flow.

At this stage the device can be placed within a suitable assay reader and the levels of analytes, for example cholesterol and blood lipids, are measured.

The housing of the assay device is usually adapted to enable it to be placed in functional communication with an assay reader. For example, the assay device may be inserted into, placed on or attached to the reader and the reader may comprise docking means, such as a slot, or alignment means to enable the assay device to be inserted, placed or attached appropriately. In this embodiment, the assay device has a 'V'-shaped cut out in the cover member which facilitates alignment of the assay device with a reader. Generally the assay device of the present invention is a disposable whilst the reader will usually be reusable.

The assay device may be used for a variety of assay processes or reactions such as immunoassays and fluorometric assays including cholesterol, lipoprotein or triglyceride assays.

An immunoassay is a biochemical test that measures the concentration of a substance in an aqueous sample, for example serum or urine. The assay utilises the reaction of an antibody or antibodies to its antigen taking advantage of the specific binding of an antibody to its antigen. Preferably monoclonal antibodies are used since they bind to one site of a particular molecule providing specific and accurate tests. Both the presence of antigen or antibodies may be measured, for example, when detecting infection the presence of antibody against the pathogen may be measured. Alternatively when measuring biological molecules such as hormones, and the like, the hormone biological molecule may acts as the antigen. The response of the aqueous fluid being measured may be compared to standards of a known concentration, for example, plotting of a standard curve on a graph. Detecting the quantity of antibody or antigen may be achieved by a variety of methods such as labelling either the antigen or antibody. By way of non-limiting example, the label may consist of an enzyme (EIA or ELISA), a radioisotope such as I-125, a magnetic label or a luminescent or fluorescent label.

Advantageously, the device of the present invention relies on capillary flow for fluid transport of low volume samples aided by use of an amphipathic or non-ionic polymer and there is therefore no need to use moving parts. Thus, the device overcomes problems of scale, economy, manufacture and mechanical failure encountered in the prior art.

An assay reader for use with the assay device of the present invention may be adapted to receive two or three assay devices, for example, from multiple patients or for multiple tests of an aqueous sample from an individual patient. Such a reader may comprise two (or more) excitation means that can be aligned with the detection zones of the assay device. 'Excitation means' are operable to excite the sample in the detection, for example, so that it fluoresces. The apparatus will also comprise at least one detection means which are operable to detect, for example, the fluorescence emitted by the sample at the detection zone(s).

Generally the excitation means comprises an illumination source operable to illuminate the sample at about 400 nm-600 nm. Accordingly the light source is preferably capable of illuminating the sample at between about 400 nm-600 nm. The illumination source may comprise one or more a bulbs, or one or more LEDs, or other sources such as a one or more lasers. Excitation wavelengths may be varied utilising at least one interference filter. The excitation means may also comprise polarising means operable to polarise light produced by the illumination source. The excitation means may also further comprise focussing means adapted to focus the light on to the sample. The focussing means may comprise a lens, or light guide such as a fibre-optic filament or optical light film (3M).

The detection means may comprise a photodiode, CCD, or photomultiplier or optical sensor, which is preferably yellow-red sensitive. Fluorescence emitted by the sample may be detected within a range including about 440 nm-650 nm depending on the dye or dyes used. The detection means should be able to detect fluorescence emitted at about 490 nm, about 495 nm, about 570 nm, about 600 nm and about 610 nm. The fluorescence may be collected by a second lens, and may pass through a polariser. Scattered excitation light may be removed by a cut-off filter(s) or band pass filter(s). For measurement of the fluorescence intensity, the current from the photodiode or the count rate from the photomultiplier may be read from an ammeter, voltmeter, or ratemeter module. Other means will be apparent to one skilled in the art.

The reader may also comprise an excitation correction system so that fluctuations of in the light source may be accounted for. The apparatus may comprise at least one fluorescence standard for use in calibrating prior to determining the concentration of an analyte or analytes. The standard may be an internal standard.

In particular embodiments the assay reader is configured to detect and measure the fluorescence intensities of a single or a plurality of assays simultaneously or in turn as the assay device enters the reader or at some time thereafter.

The reader may also comprise processing means adapted to determine the concentration of an analyte or analytes in the sample based on the fluorescence detected.

The reader may further comprise display means for displaying measurements determined from the sample, preferably as a read-out. For example, the display means may comprise an LCD screen, or may rely on a computer for powering and/or computing and/or display. In its most basic form, the display means may simply be a window in which an indication or measurement is displayed.

Usually, the assay reader is portable and advantageously, the assay device and reader may be used to carry out assays simply, rapidly and simultaneously to determine the presence/absence or concentration of an analyte from an aqueous sample such as a biological fluid. For example, a clinician with knowledge of cholesterol, lipoprotein and HDL concentrations can use the device to decide on an effective course of treatment. In addition, the assay device and reader is portable and may be used by GPs, or nurses who carry out home visits, or even as test kits for home use.

In particular embodiments, the processing means are adapted to directly determine the concentration of one or more analytes such as, cholesterol, triglycerides, HDL, LDL, VLDL and IDL in the sample based on fluorescence analysis. Alternatively, the processing means may be adapted to calculate the concentration of LDL, VLDL and IDL, in the sample based on the concentrations of total lipoprotein, cholesterol and HDL.

Use of the Device in Analysis of Cholesterol and Lipids

The following example describes a method of measuring lipoproteins in an aqueous biological sample using an assay device of the present invention.

In this example, the fluid flow pathways are coated with an amphipathic polymer, PEG, to speed up fluid transport. For lipid profiling the amphipathic polymer is also combined with a fluorescent dye such as Amplex Red, K37 or Nile Red and/or other reagents such as enzymes, laid down or printed within the fluid flow pathway(s) or within the detection zone.

The fluorescent dye(s) and/or other reagents may be printed as one or more arrays of pico-liter droplets. Suitably such an array may comprise between about 150 to 4500 droplets along a first axis by 25 to 100 droplets along a second axis. Particular sizes of array include about 3400×65 droplets, about 3000×65 droplets, about 1500×65 droplets, about 1900×65 droplets, 600×65 droplets, 450×65 droplets or about 400×65 droplets per $mm^2$. It will be apparent to one skilled in the art that, whilst these droplet densities may be varied with little effect on assay performance, it will also be apparent that conversely such densities can also be optimised to improve assay performance. For example, the droplets could also be applied as nano- or femto-liter droplets, applied as overlapping arrays, applied one (or more) on top of another, applied as discrete individual arrays, spaced apart or applied as blocks of several arrays forming an array of a larger size (i.e. additive). The array size may also be optimised with respect to a particular reagent or dye concentration for example.

When 'printing', droplets of fluorescent dye may be applied to the device at concentrations of between about 0.1 mM to 3.0 mM, more suitably, between about 0.3 to 2.5 mM, and even more suitably, between about 0.5 to 2.0 mM. Alternatively, when the device is for use with diluted blood samples, the concentration of fluorescent dye may be between about 0.8 to 1.2 mM. A useful concentration of fluorescent dye is 1.0 mM and for undiluted blood samples a useful concentration is about 2.0 mM. The dye is subsequently dried before use.

In use the sample fluid hydrates the amphipathic polymer and dilutes the fluorescent dye which can then bind to lipoproteins in the sample. When so bound the dye fluoresces under appropriate excitation. The total lipoprotein concentration in the sample may be determined using fluorescence analysis.

The method generally comprises:
(i) contacting an aqueous biological sample with at least one dye or luminophore and at least one amphipathic polymer wherein, the at least one dye or luminophore binds to at least one lipoprotein in the aqueous biological sample and when bound thereto fluoresces under appropriate excitation;
(ii) exciting the product(s) from step (i) at an excitation wavelength of between about 400 nm-620 nm;
(iii) measuring the fluorescence emission following step (ii) at a wavelength of between about 440-650 nm.

The method may be used to prepare a lipid profile from an aqueous biological sample.

By use of the term "total lipoprotein", is meant the collective concentration of at least VLDL, HDL, LDL, IDL and chylomicrons in other words, the sum of the concentrations of triglyceride and total cholesterol in a sample. By use of the term "total cholesterol", is meant the total concentration of cholesterol in a sample. By use of the term "lipid profile", is meant the concentration(s) or relative concentration(s) of lipid components (i.e. total lipoproteins and total cholesterol and triglyceride) in a sample.

Most lipids present in a blood or serum sample are bound to lipoproteins. Conventional tests conducted in clinical labs do not measure total lipoprotein. Hence, conventionally, it is required to first determine, and then add the concentration of cholesterol and cholesterol esters, to that of triglyceride to determine the total lipoprotein concentration. Conventional measurement of triglyceride in a clinical lab is subject to substantial errors because it relies on the measurement of glycerol, which circulates naturally in the blood. Advantageously, because the number (volume) of lipoprotein particles is measured directly to determine the concentration of total lipoprotein (which equates to the total lipid concentration) the cholesterol assay according to the present invention is not subject to this error. Thus, errors such as in the triglyceride concentration caused by circulating glycerol in the sample are obviated.

In their previous International patent application PCT/GB2005/004757, published as WO2006/061646, the inventors developed a simplified assay based on the use of, for example, K37 for measuring lipoproteins in a biological macromolecule that is particularly useful when a clinician wishes to quickly and efficiently obtain a lipid profile. For determining the concentration of total lipoprotein (i.e. HDL, LDL, IDL and VLDL) in a blood sample using K37 fluorescence measurements, the inventors realised that the fluorescence response from K37 bound to the various lipoprotein classes can be made substantially the same for a given total is lipoprotein concentration, i.e. total lipoprotein concentration, irrespective of its composition (i.e. the ratio of HDL:LDL:IDL:VLDL in the sample). Accordingly, it is preferred that K37 is used in such a manner that the response of fluorescence intensity is substantially linear across the range of concentrations of lipoprotein molecules that would be expected from samples that would be encountered in clinical tests.

Not wishing to be bound by any hypothesis, it is believed that the intensity of fluorescence from the fluorescent dye depends on its affinity for a particular lipoprotein molecule (HDL, LDL, IDL or VLDL) in the sample. The quantum yield of fluorescence depending on the environment within that lipoprotein molecular complex, and also the degree of fluorescence quenching caused by energy transfer between probe molecules packed closely together. Hence, in their previous application, the inventors reasoned that it would be possible to select a suitable concentration of the probe substance and excitation and emission wavelengths that may be used to make an accurate measurement of total lipoprotein by simple fluorescent measurement. The inventors further realised that such a concentration of probe would preferably balance K37's higher quantum yield in HDL compared to VLDL and LDL with its higher affinity for HDL, and therefore a higher degree of quenching within HDL to produce a constant fluorescence signal response over all lipoprotein particles.

The inventors have conducted a series of experiments to investigate whether it was possible to obtain a linear and equal relationship between the fluorescence of the probe substance, K37, and the lipoprotein concentration for each lipoprotein particle type (HDL, LDL, and VLDL), across the range of lipoprotein concentrations that would be encountered in real serum clinical samples. To their surprise, they found that there was a defined concentration of K37 and particular excitation and emission wavelengths at which there was a linear relationship between the fluorescence of K37 and lipoprotein concentration. Thus, using the methodology of their previous patent application (PCT/GB2005/004757) the skilled person may identify other suitable dyes that also demonstrate such a relationship with lipoprotein concentration.

The use of enzymes in a cholesterol assay is advantageous because cholesterol is often found in an esterified state, thus preferably cholesterol esterase is used to hydrolyse cholesterol ester to free cholesterol. Free cholesterol may then be converted to cholest-4-ene-3-one ketone by the action of cholesterol oxidase, generating hydrogen peroxide in the process. Advantageously, Amplex Red and hydrogen peroxide are converted to resorufin and water by horseradish peroxidase. Resorufin may then be detected as a fluorescent compound with an absorption maxima of about 563 nm and a peak emission wavelength of 587 nm. The total cholesterol content can be measured by exciting the sample at around 485 nm and measuring the resulting fluorescence at about 600 nm.

When an enzyme is utilised it may be provided at a level many times in excess of the ratio that would be used for measuring, for example, the enzymes Km, for example. Such a ratio may be extremely high when compared to those used in the art which are around 1:1000. Surprisingly, the combination of a difference in surface energies of the device coupled with the use of dry stabilised enzymes and optionally an amphipathic polymer enables far smaller quantities of both sample and reagent to be used. Not wishing to be bound by theory, it is believed that the difference in surface energies of the two at least partially opposing surfaces creates a circular motion within the laminar flow of the aqueous sample leading to more efficient mixing. As a result of this increase in efficiency, larger levels of enzyme may be used in smaller reaction volumes leading to yet more efficient and faster reactions than those previously possible in the methods of the prior art.

The second step for the method may comprise:
(ii) exciting the product(s) from step (i) at an excitation wavelength of between about 400 nm-520 nm.

The excitation wavelength may be between about 420 nm-480 nm or between about 440 nm-470 nm. The excitation wavelength or wavelengths used will depend on the specific fluorescent dyes being used in the assay. For Amplex Red the excitation wavelength is about 480 nm, for K37 the excitation wavelength is about 440 nm and for Nile Red the excitation wavelength is about 580 nm.

A third step of the method comprises:
(iii) measuring the fluorescence emission at a wavelength of between about 490-650 nm.

Alternatively the fluorescence emission can be measured at a wavelength of between about 520 nm-620 nm. At emission wavelengths of about 540 nm, or higher, more accurate readings for determining the total lipoprotein concentration (i.e. the concentration of HDL, IDL, LDL and VLDL, but also chylomicrons if present) may be observed. However, the preferred fluorescence emission wavelength(s) that is/are measured will depend on the specific fluorescent dyes being used in an assay. For Amplex Red the fluorescence is measured at about 600 nm, for K37 fluorescence is measured at about 495 nm and for Nile Red fluorescence is measured at about 610 nm.

It should be appreciated that the excitation and emission wavelengths need not be measured at the optimal wavelengths for each specific dye. Wavelengths may be selected that give the best separation or performance when the dyes are used either in combination or in parallel, for example when the assays are performed at the same time in a single assay device. It will be apparent that steps (ii) and (iii), excitation and detection, may also be carried out substantially simultaneously.

In addition, the concentration of triglyceride may be calculated by subtracting total cholesterol concentration from the total lipoprotein concentration. Hence, a more detailed lipid profile of the sample is thereby generated consisting of total lipoprotein concentration, total cholesterol concentration, and also triglyceride concentration, which would be useful to the clinician.

The inventors have previously discovered that a number of dyes will bind to lipoproteins and exhibit different fluorescent responses that are dependant on the particular lipoprotein bound. Fluorescent measurement of these dyes makes it possible to distinguish between the types of lipoprotein present in a sample. This is done by comparing the enhanced or reduced fluorescence caused by one type of lipoprotein in a lipoprotein mixture with the fluorescence expected from the other lipoproteins (in the absence of the specific propertied lipoprotein) as determined from a calibration curve and a known value of the total lipoprotein content. For example the fluorescent dye, Nile Red, exhibits a significantly higher fluorescence in HDL than in other lipoproteins, such as LDL and VLDL. Therefore, other fluorescent dyes (e.g. Nile Red, K37 or any other lipophilic probe that shows specificity, or fluorescence enhancement or reduction towards a particular lipoprotein), may be used to discriminate between classes or subclasses of lipoproteins in the sample.

Accordingly the method of the invention enables the determination of the concentration of a particular class, or sub-class of lipoprotein in a sample using fluorescence analysis. Generally this involves determining the concentration of a particular class or sub-class of lipoprotein by the shift in fluorescence response of a dye specific to that lipoprotein using a second and/or third fluorescent dye.

By way of example, in order to determine the HDL concentration in a sample using Nile Red, a calculation is made of the excess fluorescence from Nile Red due to the presence of HDL. Firstly, the total lipoprotein concentration (measurement "A") is measured by the linear correlation of K37 fluorescence with lipoprotein concentration (as determined by step (i)). Secondly, Nile Red fluorescence is then calibrated with LDL (and/or VLDL as the fluorescence to concentration response must be essentially the same) at various concentrations to obtain a calibration curve with slope "X" and intercept "Y". A skilled technician would know how to prepare a range of concentrations of LDL (and/or VLDL), and determine the respective fluorescence for each concentration.

Calibration curves may be constructed for a series of concentrations of HDL and a constant concentration of LDL to give slope "Z". Knowing the total lipoprotein concentration from the K37 measurement "A" and the excess Nile Red fluorescence of the unknown sample "B", the concentration of HDL "C" in the unknown sample can be determined by the following equation:

$$C=(B-(AX-Y))/Z$$

It will be appreciated that, in practice, pre-prepared or standard calibration curves may be used. Furthermore assay devices of the present invention or assay readers for use with such devices developed to generate lipid profiles may comprise internal standards and/or have processing means that will allow for automatic calculation of lipoprotein concentrations without user intervention.

Therefore, it will be appreciated that fluorescent measurements may be used for determining the concentration of HDL, VLDL (by calculation), LDL (by calculation), total lipoprotein, triglycerides (by calculation) and also total cholesterol. All these parameters may be determined simultaneously, in parallel, by exciting and measuring fluorescence over a similar range of wavelengths. As discussed above, this is a considerable improvement over conventional assays, which have to be carried out separately, and often in dedicated laboratories, causing a delay in the generation of results. In addition, the fact that multiple lipid parameters can be measured at the same time considerably simplifies the instrumentation required to carry out the measurements.

The lipid profile generated includes the determination of the concentration of cholesterol bound to LDL in the sample. It is especially advantageous to know the LDL cholesterol concentration as it is highly atherogenic. Hence, the method provides a multi-readout of at least three, preferably four or five, or more parameters of the lipid composition in the sample. Furthermore, it is possible to calculate/estimate the concentration of Cholesterol-VLDL-Cholesterol from the triglyceride concentrations, as it is generally assumed that most of the triglycerides are carried in VLDL and the cholesterol component of VLDL is 20%. This is particularly advantageous for helping the clinician to decide on a suitable course of treatment.

EXAMPLES

The invention will now be described with reference to the following examples which describe the complete exposition of embodiments of the invention as described above.

Example 1

Total Cholesterol Assay

The assay utilizes a triple enzyme system capable of converting one molecule of cholesterol or cholesterol ester into a molecule of hydrogen peroxide ($H_2O_2$). The hydrogen peroxide generated is then used to oxidize the dye Amplex Red (non-fluorescent) to generate the highly fluorescent product Resorufin.

Stabilization of Enzymes onto Plastic

The total cholesterol assay uses the following enzymes and dye:

Cholesterol Esterase (3.1.1.13)
Cholesterol Oxidase (1.1.3.6)
Horseradish Peroxidase (1.11.1.7)
Amplex Red: 10-acetyl-3,7-dihydroxyphenoxazine Enzymes were stabilized onto plastic using Gafquat as a stabilizing agent. The three enzymes is were added to a solution of 0.01M potassium Phosphate buffer, pH 7.0. Final activity of each enzyme was measured at 200 U/ml of buffer. The solution was then diluted 1:1 with Gafquat (highly positively charged polymer) formulation and 5 ul of the resulting solution was deposited onto a plastic surface and dried at 30° C. in the presence of silica gel for 2 hours. The process resulted in a dry enzyme bio-surface, with 0.5 U of each enzyme deposited.

Assay Procedure—Utilising 1/80 Sample Dilution

Two approaches were taken, a) reaction of cholesterol sample (plasma) with dried enzymes and Amplex Red in solution, b) reaction of cholesterol sample with both dried enzymes and dried stabilized Amplex Red dye:

(a) Reaction of Cholesterol Sample (Plasma) with Dried Enzymes and Amplex Red in Solution.

Dilution buffer A: 4.16 mM Amplex Red, 10 mM Cholic acid, 0.2% Triton X-100 in Dulbecco phosphate buffered saline pH 7.2.

The sample to be assayed was first diluted 1 part into 80 parts of dilution buffer A, then 50 ul of the diluted sample was used to reconstitute and activate the dried tri-enzyme mix (previously stabilized as described above) in the sample assay chamber.

The cholesterol content was measured by exciting the sample mix at 480 nm and measuring the resulting fluorescence at 600 nm. Cholesterol concentration was determined directly through measurement of the steady state fluorescence after 40 seconds, or Vmax (maximal rate of substrate generation). Each evaluation was made by reference to assay standard data.

(b) Reaction of Cholesterol Sample (Plasma) with Both Dried Enzymes and Amplex Red.

Dilution buffer B: 10 mM Cholic acid, 0.2% Triton X-100 in Dulbecco phosphate buffered saline pH 7.2.

This procedure is similar to the above process. However, in this process the Amplex Red dye was dried in the flow path along with the tri-enzyme mix. Firstly, one defined region of the assay chamber was coated with 0.5 U Cholesterol Esterase (3.1.1.13), 0.5 U Cholesterol Oxidase (1.1.3.6) and 0.5 U Horseradish Peroxidase (1.11.1.7) as described above. A second and separate region of the assay chamber was then coated with 10 µl of Amplex Red/PEG2000 solution and dried at 30° C. in the presence of silica gel for 2 hr. The dye coating solution was composed of 5.35 mg/ml Amplex Red, 5% w/v PEG2000 in dimethylsulphoxide (DMSO).

The sample to be assayed was diluted, 1 part into 80 parts of dilution buffer B, and 50 ul of the diluted sample was used to reconstitute and activate the dried Amplex Red dye and tri-enzyme mix in the sample assay chamber.

The cholesterol content was measured by exciting the sample mix at 480 nm and measuring the resulting fluorescence at 600 nm. The cholesterol concentration was again determined directly through either the measurement of Vmax (maximal rate of substrate generation) or steady state fluorescence after 40 seconds. Each evaluation was made by reference to assay standard data.

Both assays were determined to be capable of determining clinically relevant cholesterol levels of between 2-11 mM.

Assay Procedure—Utilising Undiluted Sample

Neat biological samples were assayed by applying the sample to a borosilicate filter impregnated with anti-HSA antibody located within the consumable device, which serves to filter and direct the sample to an appropriate 200 µm deep read or detection area. Pre-coating of the read area firstly with 400×65 pico-liter droplets of enzyme reagent per mm², followed by 600×65 pico-liter droplets of dye reagent per mm2 and 450×65 pico-liter droplets of inhibitor reagent per mm2 facilitates rapid flow of the sample into the read area. Subsequent excitation of the sample at 480 nm (10 nm band pass) generates fluorescence that can be detected through a 600 nm (10 nm band pass) filter to allow the Total Cholesterol content of the sample to be determined by reference to suitable standard measurements.

Enzyme Reagent: Cholesterol Esterase, Cholesterol Oxidase and Horseradish Peroxidase, each dissolved in a Gafquat stabiliser mix at 200 units per ml.

Detergent solution: 1.63 g Cholic Acid, 10 g Polyethylene glycol 2000, 800 ul Triton X-100 and is 253.3 ul of Diethyl Maleate is dissolved in dimethylformamide (DMF) and the final volume adjusted to 40 ml.

Dye Reagent: 5 mg of Ampliflu Red solid added to 480 µl of detergent solution.

Inhibitor Reagent: 260 mg sodium azide and 912.92 mg potassium phosphate dibasic trihydrate is dissolved in water and the final volume adjusted to 40 ml.

Example 2

Total Lipid Assay

The K37 dye was dissolved in DMF to a final concentration of 1.0 mM. Next 5% w/v PEG 2000 was dissolved into the dye solution and 60 nanoliters of the resulting solution was deposited onto a plastic surface and dried by removing the solvent under vacuum for 1 hour at room temperature in the dark.

Assay Procedure—Utilising Diluted Sample

The sample to be assayed (plasma) was first diluted 1 part into 80 parts phosphate buffered saline containing 50 mM Sodium Octanoate, pH 7.4.

5 µl of diluted plasma sample was applied to the dried dye which spontaneously hydrated. The Total lipid content was measured by exciting the sample at 440 nm (10 nm bandpass) and measuring the resulting fluorescence passing through a 495 nm filter (10 nm bandpass). The total lipid content was determined empirically by reference to known standards.

Assay Procedure—Utilising Undiluted Sample

Neat biological samples are assayed by applying the sample to a borosilicate filter impregnated with anti-HSA antibody located within a consumable device, which serves to filter and direct the sample to an appropriate 200 µm deep read area. Pre-coating of the read area with 3000×65 pico-liter droplets of 2 mM K37/5% (w/v) PEG2000 in DMF per mm² facilitates rapid flow of the sample into the read area and spontaneous partitioning of dye into the lipoproteins contained within the sample. Subsequent excitation of the sample at 440 nm (10 nm band pass) generates fluorescence that can be detected through a 495 nm (10 nm band pass) filter to allow the total lipid content of the sample to be determined by reference to suitable standard measurements.

Example 3

HDL Cholesterol Assay

Nile Red was dissolved in DMF to a final concentration of 0.5 mM. Next 5% w/v PEG 2000 was dissolved into the dye solution and 60 nanoliters of the resulting solution was deposited onto a plastic surface and dried by removing the solvent under vacuum for 1 hour at room temperature in the dark.

Assay Procedure—Utilising Diluted Sample

The sample to be assayed (plasma) was first diluted 1 part into 80 parts phosphate buffered saline containing 50 mM Sodium Octanoate, pH 7.4.

5 µl of diluted plasma sample was applied to the dried dye which spontaneously hydrated. The HDL cholesterol content was measured by exciting the sample at 580 nm (10 nm bandpass) and measuring the resulting fluorescence passing through a 610 nm filter (10 nm bandpass). HDL cholesterol content was calculated by use of the algorithm described in the main specification. An equivalent assay may also be performed utilising whole, undiluted blood.

Assay Procedure—Utilising Undiluted Sample

Neat biological samples are assayed by applying the sample to a borosilicate filter impregnated with anti-HSA antibody located within a consumable device, which serves to filter and direct the sample to an appropriate 200 µm deep read area. Pre-coating of the read area with 3400×65 picoliter droplets of 0.5 mM Nile Red/5% (w/v) PEG2000 in DMF per $mm^2$ facilitates rapid flow of the sample into the read area and spontaneous partitioning of dye into the lipoproteins contained within the sample. Subsequent excitation of the sample at 580 nm (10 nm band pass) generates fluorescence that can be detected through a 610 nm (10 nm band pass) filter to allow the HDL-c content of the sample to be determined by reference to suitable standard measurements.

Manipulating the data from the three tests described in examples 1, 2 and 3 provides the following:
Measurement of total cholesterol—ie test (1)
Measurement of total lipid concentration—ie test (2)
Measurement of HDL cholesterol—ie test (3)
Calculated value of triglyceride—ie tests (2) less (1)
Calculated value of VLDL—ie value of triglyceride/2.2
Calculated value of LDL—ie determined by Friedwald equation

Example 4

Use of PEG to Enhance Lateral Fluid Flow in Near Horizontal Capillaries

Glass capillaries 100 mm long and having internal diameters of 2 mm, 1 mm and 0.5 mm were either left untreated, detergent-treated or coated with PEG. The detergent treated capillaries were prepared by washing with a solution of virkon and Triton X100 5% followed by drying. PEG treated capillaries were prepared by flowing 5% (w/v) PEG in chloroform through the capillaries, allowing the surplus to drain followed by drying.

Treated and un-treated capillaries were fixed in a near-horizontal position (about 10° upward flow angle) and the tips of the capillaries were submerged in water. The distance travelled and flow rate of water moving into each capillary was measured:
Untreated Capillaries:
2 mm—reached 20 mm in ~30 seconds
1 mm—reached 90 mm in 15 seconds
0.5 mm—reached end of tube (100 mm) in 18 seconds
Detergent Treated Capillaries
2 mm—reached 20 mm in ~20 seconds
1 mm—reached 90 mm in 12 seconds
0.5 mm—reached end of tube (100 mm) in 15 seconds
PEG-Coated Capillaries:
2 mm—reached 80 mm in ~20 seconds
1 mm—reached end in 1-2 seconds
0.5 mm—reached end of tube (100 mm) in 1-2 seconds This data demonstrates that capillary fluid flow in PEG-coated capillaries is approximately four times faster than in detergent treated capillaries and approximately six times faster than in untreated capillaries.

Capillaries were made hydrophobic by treating with a siliconising agent (dimethyl dichlorosilane) and baking at 120° C. Water did not enter the lumen of these capillaries. Coating the hydrophobic capillaries with PEG (as above) restored the fluid flow conditions comparable to PEG coated capillaries without silation. In some of the experiments where the surface coating of PEG was discontinuous the fluid flow stopped at the break in the PEG coating.

Experiment 5

Use of PEG to Enhance Fluid Flow in Vertical Capillaries

Capillaries having a length of 100 mm and diameters of 2 mm, 1 mm, or 0.5 mm were treated as described above. The capillaries were fixed in a vertical position and the tips of the capillaries were submerged in water. The Height reached by water in the vertical capillary tubes was measured:
Untreated Tubes:
2 mm diameter—9 mm
1 mm diameter—22 mm
0.5 mm diameter—51 mm
Detergent Treated Tubes
2 mm diameter—10 mm
1 mm diameter—22 mm
0.5 mm diameter—53 mm
PEG-Coated Tubes
2 mm diameter—11 mm
1 mm diameter—25 mm
0.5 mm diameter—54 mm Water did not enter hydrophobic silated capillary tubes at all. By coating the silated capillaries with PEG the capillary flow heights were restored and similar to those of unsilated PEG-coated capillaries.

The theoretical maximum heights at sea level using the equation $h = 2\gamma \cos\theta / \rho g r$, where h is the height (m); $\gamma$ is the surface tension; $\theta$ the contact angle; $\rho$ is the density; g is acceleration due to gravity; and r is the radius of the tube (m) are:
14 mm at 2 mm ID
28 mm at 1 mm ID
56 mm at 0.5 mm ID

Example 6

Reproducibility of Transfer and Long-Term Stability

The reproducibility of transfer and long-term stability of hydrophobic molecule (i.e. dye)/amphipathic polymer mixture was measured as follows:

PEG with a molecular weight of 2000 Da was dissolved into a solution of hydrophobic dye (either Nile Red or K37) in dimethylformamide (DMF), at a concentration of 5% w/v. PEG/dye films were made by depositing 25 µl of PEG/dye solution in DMF in a 5 ml glass vial. The solution was spread over the base of the vial and then placed in a vacuum chamber for one hour to evaporate the solvent.

Reproducibility of transfer was measured by comparing the fluorescence intensity of dye in DMF added to a lipoprotein solution with the fluorescence intensity of an identical lipoprotein solution in which the dye/PEG film was re-dissolved. Reproducibility was calculated by obtaining the Coefficients of variation (CVs) of fluorescence intensities from ten dye/PEG films in lipoprotein solutions.

Stability was evaluated by laying down films for long-term storage, and measuring the fluorescence intensity of these films when re-dissolved in lipoprotein solutions after varying storage times. Films were stored in the dark under a range of conditions: in air with no desiccating agent, in air in the presence of silica gel, and under vacuum in the presence of silica gel. Films were stored under these conditions at temperatures of both 20 and 37° C.

The fluorescence intensities for dyes in lipoprotein solutions dissolved in DMF or in PEG films were determined:

|  | K37 | Nile Red |
|---|---|---|
| From DMF | 268000 | 297000 |
| From PEG film | 269000 | 296000 |

Identical fluorescence intensity readings (within 0.5%) were obtained for PEG films as were obtained when adding dye dissolved in DMF. The reproducibility of fluorescence readings from dye/PEG films with lipoprotein was calculated:

|  | K37 | Nile Red |
|---|---|---|
| Film 1 | 6.23E+05 | 4.27E+05 |
| Film 2 | 6.25E+05 | 4.27E+05 |
| Film 3 | 6.24E+05 | 4.29E+05 |
| Film 4 | 6.25E+05 | 4.26E+05 |
| Film 5 | 6.24E+05 | 4.27E+05 |
| Film 6 | 6.26E+05 | 4.30E+05 |
| Film 7 | 6.23E+05 | 4.30E+05 |
| Film 8 | 6.25E+05 | 4.28E+05 |
| Film 9 | 6.22E+05 | 4.28E+05 |
| Film 10 | 6.22E+05 | 4.26E+05 |
| Mean | 6.24E+05 | 4.28E+05 |
| SD | 1370.32 | 1475.73 |
| CV (%) | 0.22 | 0.34 |

CVs of less than 0.5% were obtained for both dyes.

Stability Measurements

| Time | K37 in DMF 20 C. | K37 in PEG 20 C. in air | K37 in PEG 20 C. in air over silica gel | K37 in PEG 20 C. in vac over silica gel | K37 in PEG 37 C. in air | K37 in PEG 37 C. in air over silica gel | K37 in PEG 37 C. in vac over silica gel |
|---|---|---|---|---|---|---|---|
| Zero | 138630 | 139320 | 137241 | 138624 | 137440 | 138317 | 136942 |
| 1 week | 137500 | 137113 | 137840 | 138801 | 137640 | 136922 | 136817 |
| 4 weeks | 134890 | 134641 | 133980 | 134202 | 135016 | 135412 | 134097 |
| 8 weeks | 135254 | 136021 | 135972 | 136671 | 135926 | 136201 | 135552 |
| % CV | 1.31 | 1.44 | 1.25 | 1.56 | 0.92 | 0.90 | 0.98 |

| Time | NR in DMF 20 C. | NR in PEG 20 C. in air | NR in PEG 20 C. in air over silica gel | NR in PEG 20 C. in vac over silica gel | NR in PEG 37 C. in air | NR in PEG 37 C. in air over silica gel | NR in PEG 37 C. in vac over silica gel |
|---|---|---|---|---|---|---|---|
| Zero | 495197 | 496130 | 494590 | 495760 | 494118 | 494241 | 494829 |
| 1 week | 495002 | 495600 | 494802 | 494400 | 494636 | 493907 | 494621 |
| 4 weeks | 493128 | 492686 | 493440 | 493662 | 494017 | 492506 | 492906 |
| 8 weeks | 493492 | 494620 | 494525 | 493986 | 493920 | 492500 | 493650 |
| % CV | 0.21 | 0.31 | 0.12 | 0.19 | 0.06 | 0.19 | 0.18 |

CONCLUSIONS (1) Dyes incorporated into PEG films fully re-dissolve when reconstituted with aqueous solutions, and give the same fluorescence intensities as dyes added in organic solvents.
(2) The dye/PEG films are reproducible and films made up in the same way result in the same fluorescence intensity.
(3) The dye/PEG films are stable for at least 52 weeks when stored under the harshest storage conditions tested (37° C., no desiccant).

Example 7

Comparison of Amphipathic/Non-Ionic Polymers

Borosilicate capillaries (100 mm long, 1 mm ID from Composite Metal Services Ltd—CV1012) were coated by drawing up 7 mm of a 5% polymer solution in various solvents and rocked until dry. The solvent used was dependent on solubility with chloroform favoured because of its high evaporation rate.

Experiments on the coated capillaries were performed in triplicate and an uncoated capillary was run each time as a reference. The 4 capillaries were held vertical on a lined reference card by 2 slots cut into the card for each capillary. The ends of the capillaries extended exactly 7 mm past the bottom of the card.

The experiment was videoed using a Sunkwang High Resolution Low Lux Color Camera connected to a Winnov 500050G V1000+OV PC card and the program Videum Capture was used to capture and analyse the data. The frame rate was set at 5 frames per second (to avoid dropped frames) unless otherwise stated. The flow liquid (10-4 M Rose Bengal in water) was contained in a flat bottomed watch glass and the card simply lowered end-on until the bottom of the card came to rest on the walls of the watch glass. Capillaries were submerged in the flow liquid to a depth of 2 mm. This produced a gap of 5 mm to the bottom of the card, 9 mm from the bottom of the card to the first line and a further 6 mm to the second line up the card. Flow rates were calculated by counting how many frames elapsed for the 9 mm of travel between the bottom of the card and the first line.

TABLE 1

Performance of polymer coatings/solvent systems in water column height and capillary flow rate.

| Coating | Solvent | Average water column height mm | STDEV on column height | Average flow rate mm/s | STDEV on average flow rate mm/s | Fastest rate mm/s |
|---|---|---|---|---|---|---|
| PEG2000 | Chloroform | 17.8 | 0.76 | 21.9 | 3.3 | 25.7 |
| PEG2000 | DMF | 19.8 | 1.89 | 27.6 | 28.1 | 60 |
| PEG2000 | Water | 13.5 | 5.77 | 29.7 | 37.2 | 72 |
| PEG6000 | Chloroform | 19.3 | 0.76 | 21.5 | 4.8 | 25.7 |
| PEG12,000 | Chloroform | 16.5 | 0.87 | 7.6 | 3.3 | 9.5 |
| PEG20,000 | Chloroform | 15.3 | 1.04 | 3.2 | 1.6 | 4.9 |
| Triton X100 | Water | 14.2 | 1.04 | 7.9 | 2.2 | 10 |
| Carboxymethyl cellulose | Water | 18.0 | * | 180 | * | 180 |
| 0,0'-Bis(2-aminoethyl) polyethylene glycol 2000 | Chloroform | 17.0 | 3.5 | 38.8 (52.5) | 25.0 (10.6) | 60 |
| PEG methyl ether 5000 | Chloroform | 17.8 | 1.26 | 2.4 | 0.2 | 2.6 |

* = a result from a single capillary
( ) = a result from 2 out of 3 capillaries as capillary had a column height below the first line of the card and was therefore estimated.

Figure 5:
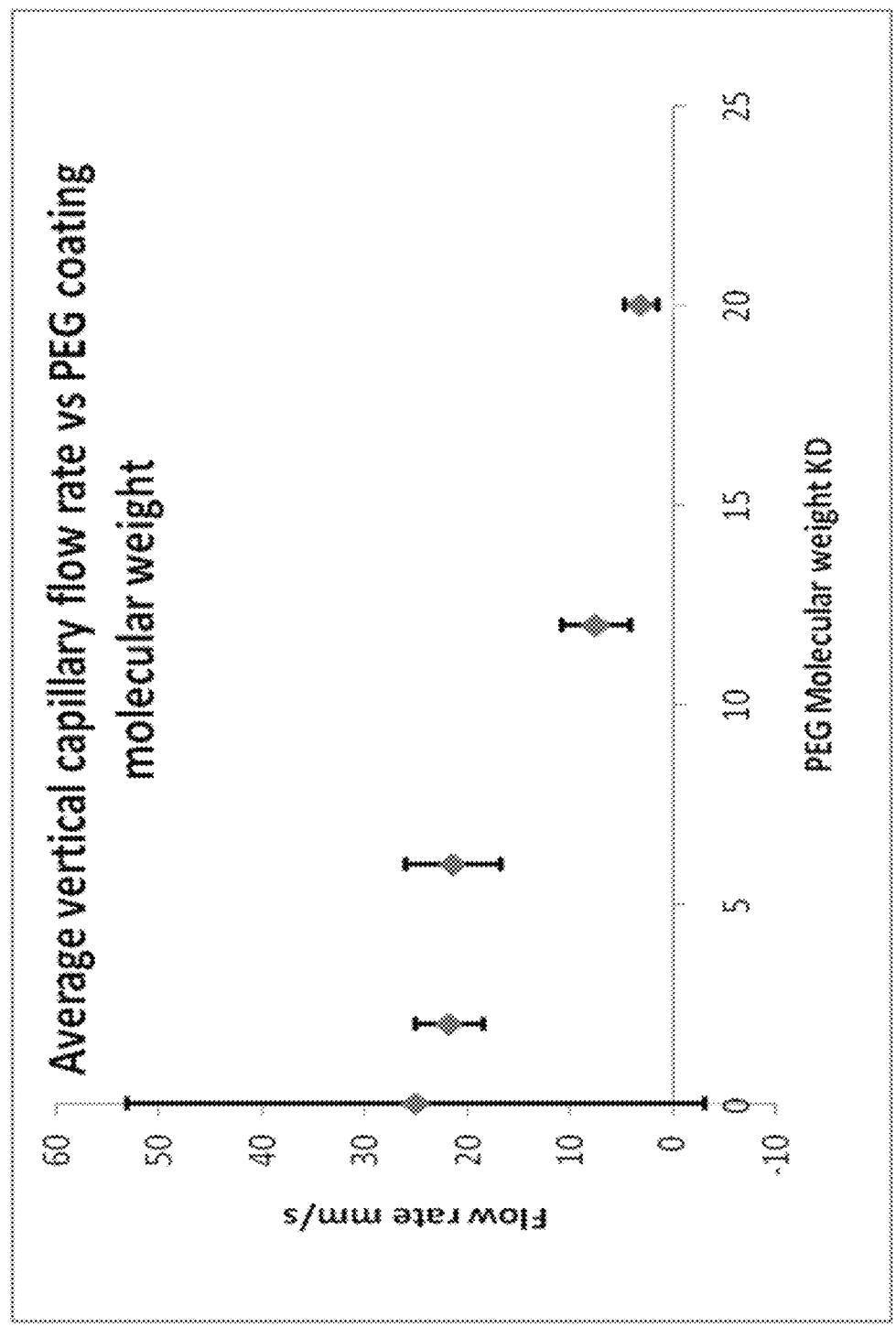
FIG. 5 illustrates the effect of molecular weight of PEG on vertical flow rate. Error bars indicate +/−1 standard deviation (uncoated capillary tubes and their 1 order of standard deviation are shown at zero molecular weight).

FIG. 5 illustrates the effect of molecular weight of PEG on vertical flow rate.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

The invention claimed is:

1. An assay device for detecting the presence or quantity of an analyte residing in an aqueous sample, the device comprising:
a non-porous support; and
at least one flow path along which an aqueous sample can travel, wherein the at least one flow path comprises, on the non-porous support, a non-phase-separated combination of at least one amphipathic polymer and at least one hydrophobic probe, reporter or reagent, wherein, in use, the at least one amphipathic polymer dissolves in the aqueous sample and increases mixing and interaction between the at least one hydrophobic probe, reporter or reagent and the aqueous sample for any degree of water solubility of the at least one probe, reporter or reagent, including water-insolubility, and promotes and/or controls fluid flow along the at least one flow path.

2. The device of claim 1 wherein the result and/or progress of a reaction is determined by means of optical measurement.

3. The device of claim 1 wherein the amphipathic polymer is polyethylene glycol (PEG).

4. The device of claim 3 wherein the amphipathic polymer is polyethylene glycol with a molecular weight of from 1000 Da to 20,000 Da.

5. The device of claim 4 wherein the amphipathic polymer is polyethylene glycol with a molecular weight of from 1000 Da to 6000 Da.

6. The device of claim 1 wherein the amphipathic polymer is printed and/or sprayed onto a surface of the device.

7. The device of claim 6 wherein the amphipathic polymer forms one or more arrays of nano-, pico- or femto-liter droplets.

8. An assay device comprising:
(i) at least one application area suitable for application of an aqueous sample to the device;
(ii) at least one hydrophobic probe, reporter or reagent wherein, in use the at least one hydrophobic probe, reporter or reagent is able to react with an analyte residing in the aqueous sample;
(iii) at least one test area wherein, in use the result and/or progress of a reaction between the analyte and the at least one hydrophobic probe, reporter or reagent may be determined; and
(iv) at least one flow path being in fluid communication with the at least one application area and the at least one test area;
wherein the at least one flow path comprises, on a non-porous support, a non-phase-separated combination of at least one amphipathic polymer and the at least one hydrophobic probe, reporter or reagent, wherein, in use, the at least one amphipathic polymer dissolves in the aqueous sample and increases mixing and interaction between the at least one hydrophobic probe, reporter or reagent and the aqueous sample for any degree of water solubility of the at least one hydrophobic probe, reporter or reagent, including water-insolubility, and promotes and/or controls fluid flow along the at least one flow path.

9. The device of claim 8 which comprises at least three test areas and at least three flow paths wherein, a first flow path is in fluid communication with the application area and a first test area, a second flow path is in fluid communication with the application area and a second test area and a third flow path is in fluid communication with the application area and a third test area.

10. The device of claim 9 wherein a first flow path comprises Amplex Red, a second flow path comprises K37 and a third flow path comprises Nile Red.

11. The device of claim 9 wherein a first test area comprises Amplex Red, a second test area comprises K37 and a third test area comprises Nile Red.

12. The device of claim 9 wherein the first flow path further comprises cholesterol esterase, cholesterol oxidase and horse radish peroxidise.

13. The device of claim 9 wherein the first test area further comprises cholesterol esterase, cholesterol oxidase and horse radish peroxidise.

14. The device of claim 9 wherein the application area comprises the at least one probe, reporter or reagent selected from the group consisting of Amplex Red, K37, Nile Red, cholesterol esterase, cholesterol oxidase and horse radish peroxidise.

15. The device of claim 8 wherein the at least one hydrophobic probe, reporter or reagent further comprises a stabilizing agent.

16. The device of claim 15 wherein the stabilizing agent is a copolymer of vinyl pyrrolidine and dimethylaminoethyl methacrylate.

17. The device of claim 8 wherein the at least one probe, reporter or reagent is selected from the group consisting of Amplex Red, K37, Nile Red, cholesterol esterase, cholesterol oxidase and horse radish peroxidase.

18. A method of producing an assay device for detecting the presence or quantity of an analyte residing in an aqueous sample, the method comprising:
- dissolving an amphipathic polymer in a solvent;
- dissolving at least one hydrophobic probe, reporter or reagent in a solvent that is miscible with the amphipathic polymer;
- drying the dissolved amphipathic polymer and the dissolved at least one hydrophobic probe, reporter or reagent in at least one flow path on a non-porous support, thereby forming a non-phase-separated combination;
- wherein, when an aqueous sample travels along the at least one flow path, the at least one amphipathic polymer dissolves in the aqueous sample and increases mixing and interaction between the at least one hydrophobic probe, reporter or reagent and the aqueous sample for any degree of water solubility of the at least one hydrophobic probe, reporter or reagent, including water-insolubility, and promotes and/or controls fluid flow along the at least one flow path.

19. An assay device produced by the method of claim 18.

* * * * *